United States Patent
O'Mahony et al.

(10) Patent No.: US 7,135,008 B2
(45) Date of Patent: *Nov. 14, 2006

(54) METHOD AND APPARATUS FOR ULTRAFILTRATION UTILIZING A PERIPHERAL ACCESS DUAL LUMEN VENOUS CANNULA

(75) Inventors: John J. O'Mahony, Minnetonka, MN (US); Steven Bernard, Andover, MN (US); Sean P. Skubitz, Shoreview, MN (US)

(73) Assignee: CHF Solutions, Inc., Brooklyn Park, MN (US)

( * ) Notice: Subject to any disclaimer, the term of this patent is extended or adjusted under 35 U.S.C. 154(b) by 320 days.

This patent is subject to a terminal disclaimer.

(21) Appl. No.: 10/724,620

(22) Filed: Dec. 2, 2003

(65) Prior Publication Data
US 2005/0119597 A1    Jun. 2, 2005

(51) Int. Cl.
*A61M 1/36* (2006.01)
*A61M 37/00* (2006.01)
*C02F 1/44* (2006.01)
*B01D 61/00* (2006.01)
*B01D 24/00* (2006.01)

(52) U.S. Cl. ............... 604/4.01; 604/5.04; 604/5.01; 604/6.09; 604/6.16; 422/44; 422/272; 210/646; 210/650; 210/321.6

(58) Field of Classification Search ............... 604/4.01, 604/5.01–5.04, 6.04, 6.09, 6.11, 6.16, 7, 8, 604/27–29, 523, 264, 500, 507, 271–272; 210/600, 634, 645–647, 650, 651, 739–741, 210/321.6–8; 623/3.1, 3.26; 422/44; 600/433, 600/435

See application file for complete search history.

(56) References Cited

U.S. PATENT DOCUMENTS

| | | | |
|---|---|---|---|
| 5,188,593 A * | 2/1993 | Martin | 604/43 |
| 5,928,181 A * | 7/1999 | Coleman et al. | 604/8 |
| 5,989,206 A | 11/1999 | Prosi et al. | |
| 6,287,608 B1 | 9/2001 | Levin et al. | |
| 6,461,321 B1 * | 10/2002 | Quinn | 604/43 |
| 6,514,226 B1 | 2/2003 | Levin et al. | |
| 6,533,747 B1 | 3/2003 | Polaschegg et al. | |
| 6,579,259 B1 * | 6/2003 | Stevens et al. | 604/96.01 |
| D476,730 S | 7/2003 | O'Mahony et al. | |
| D477,867 S | 7/2003 | O'Mahony et al. | |
| 6,585,675 B1 | 7/2003 | O'Mahony et al. | |
| D479,320 S | 9/2003 | O'Mahony et al. | |

(Continued)

OTHER PUBLICATIONS

Brian E. Jaski et al., "Peripherally Inserted Veno-Venous Ultrafiltration For Rapid Treatment of Volume Overloaded Patients", Journal of Cardiac Failure vol. 9, No. 3, 2003, pp. 227-231.

*Primary Examiner*—Tatyana Zalukaeva
*Assistant Examiner*—Leslie R. Deak
(74) *Attorney, Agent, or Firm*—Nixon & Vanderhye P.C.

(57) ABSTRACT

Method and apparatus for the extracorporeal treatment of blood by utilizing a peripherally inserted dual lumen catheter assembly for the continuous removal and return of blood for renal replacement treatment, in particularly, treatment of congestive heart failure and fluid overload by ultrafiltration. A catheter is inserted in a peripheral vein and maneuvered upward through the vascular system to access the reservoir of blood in the large or great veins for continuous blood withdrawal and treatment. Air-tight connectors are incorporated in the catheter assembly to overcome the untoward effects of negative pressure in blood withdrawal.

32 Claims, 17 Drawing Sheets

U.S. PATENT DOCUMENTS

| | | |
|---|---|---|
| 6,685,664 B1 | 2/2004 | Levin et al. |
| 6,689,083 B1 | 2/2004 | Gelfand et al. |
| 6,706,007 B1 | 3/2004 | Gelfand et al. |
| 6,773,412 B1 | 8/2004 | O'Mahony et al. |

* cited by examiner

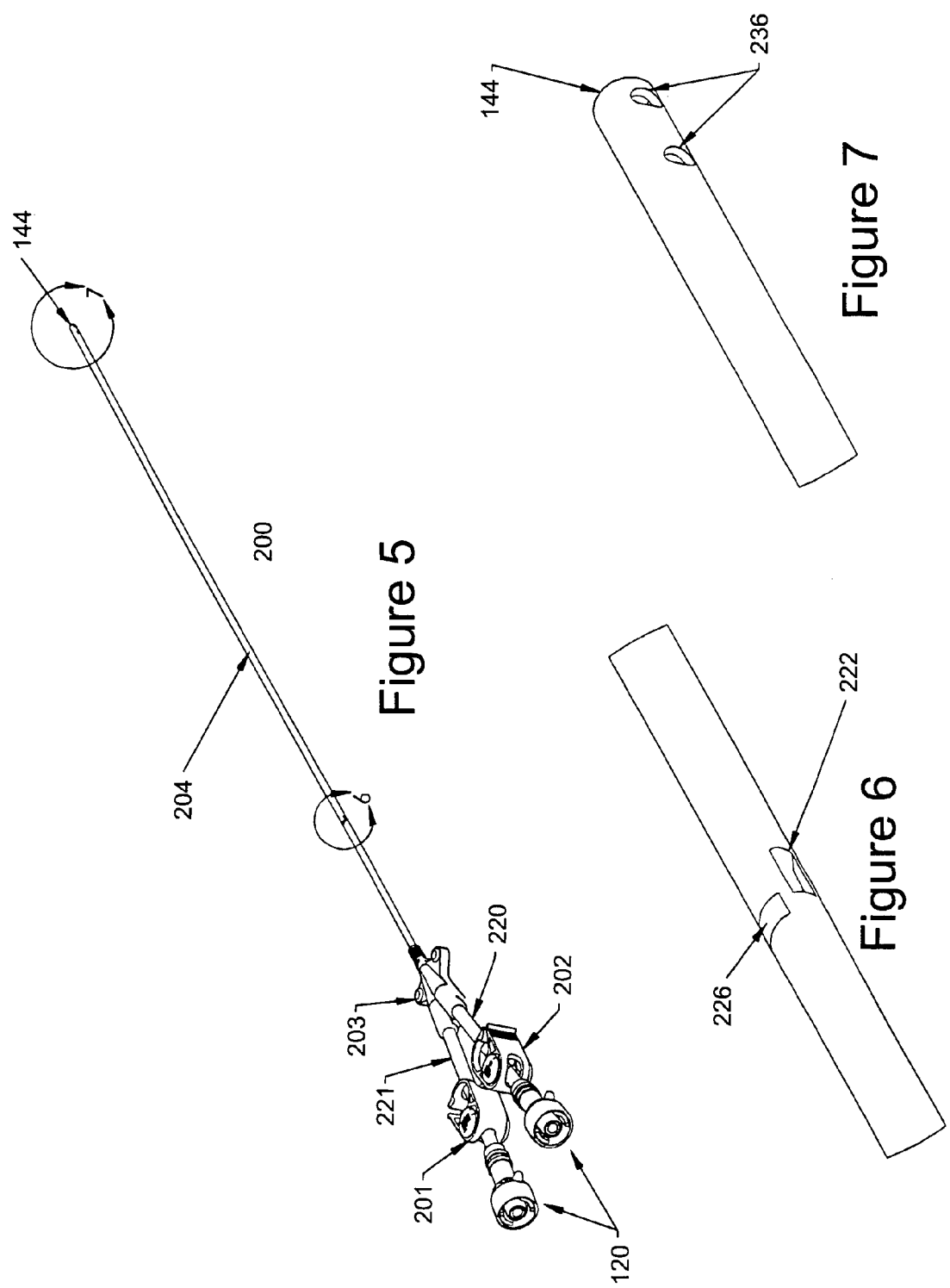

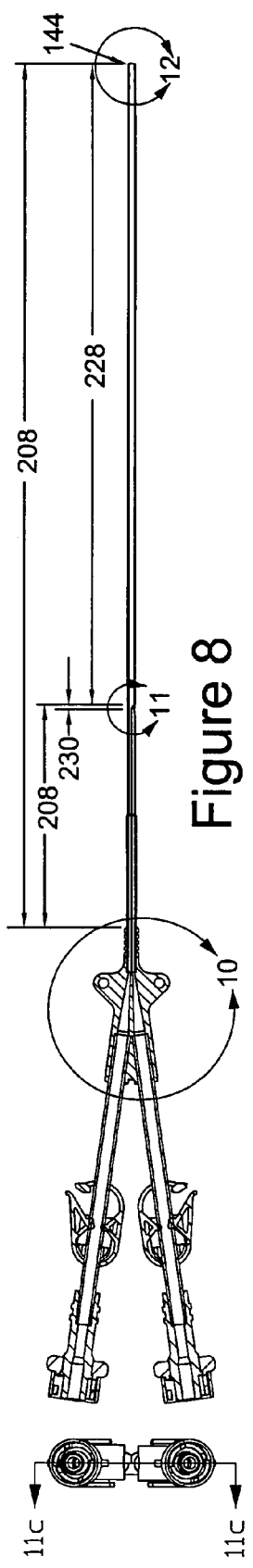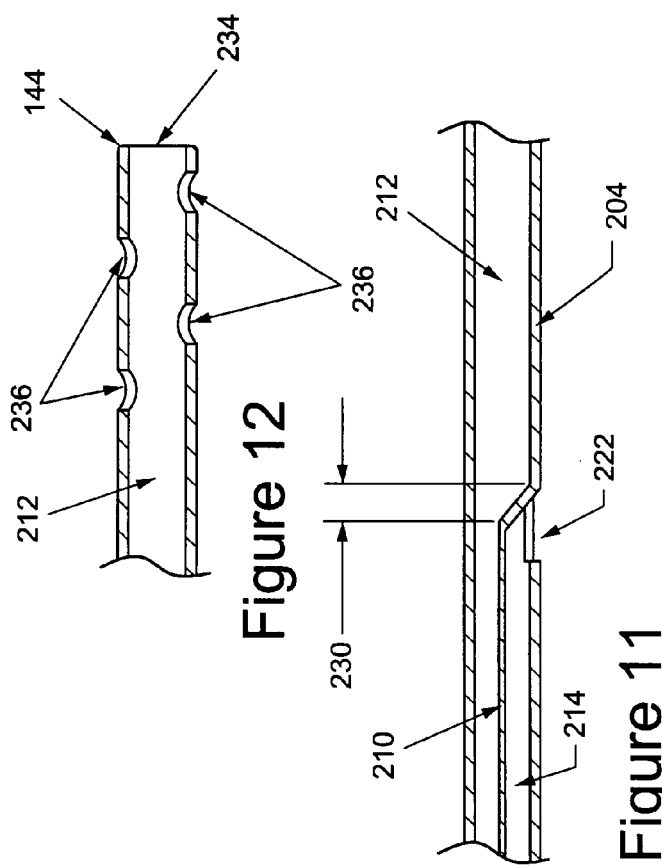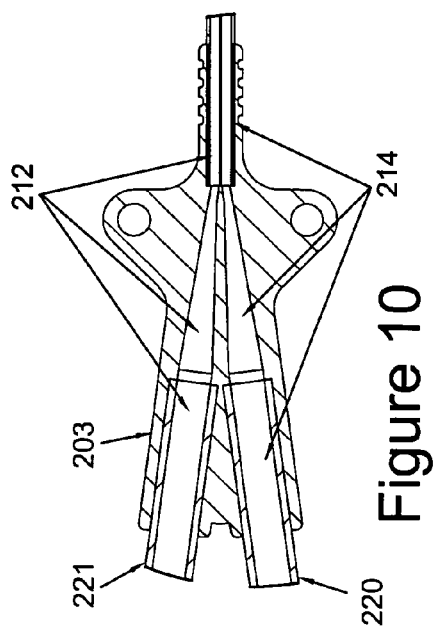

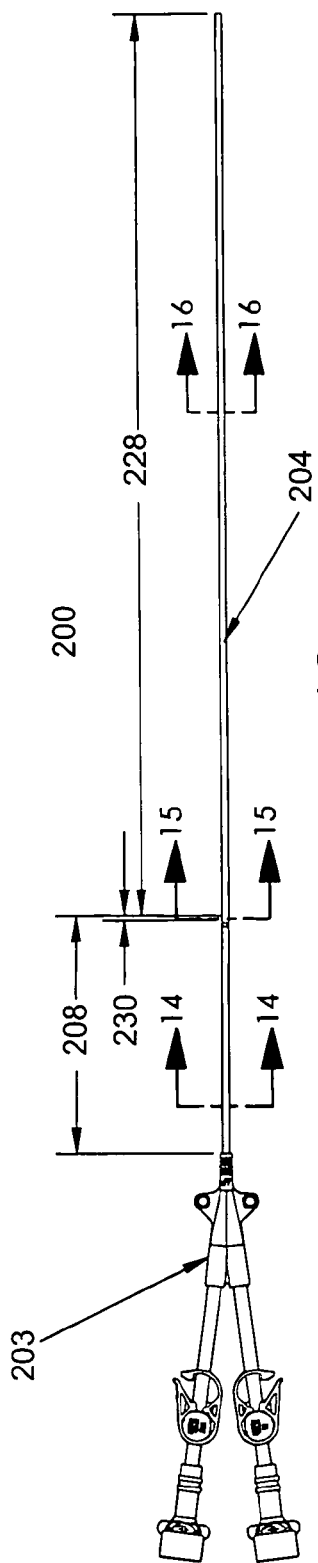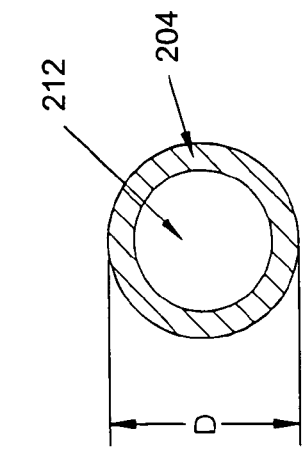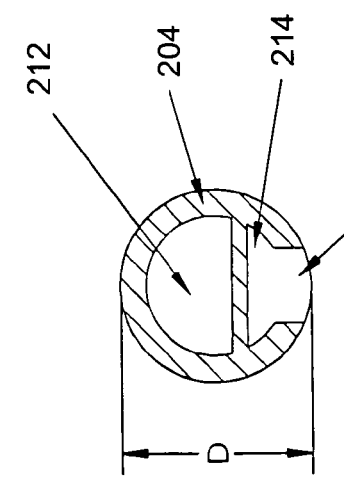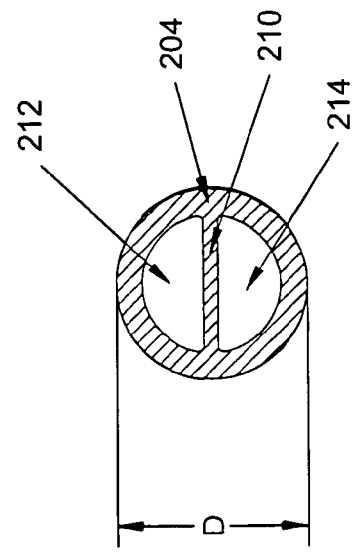

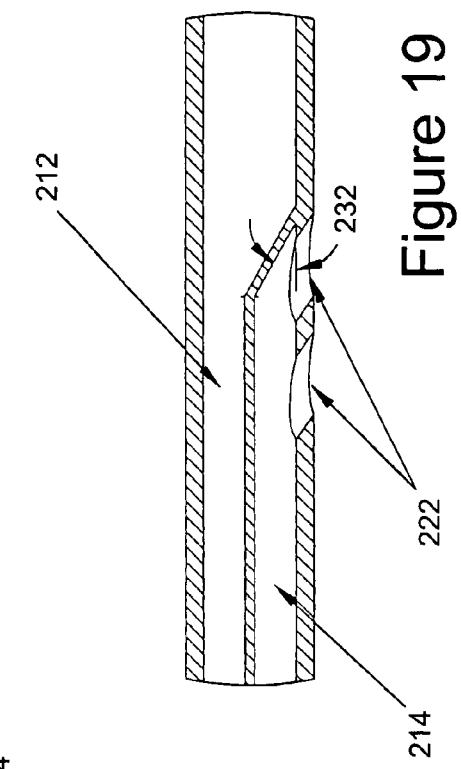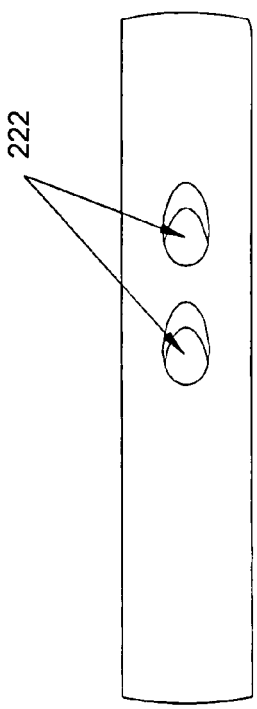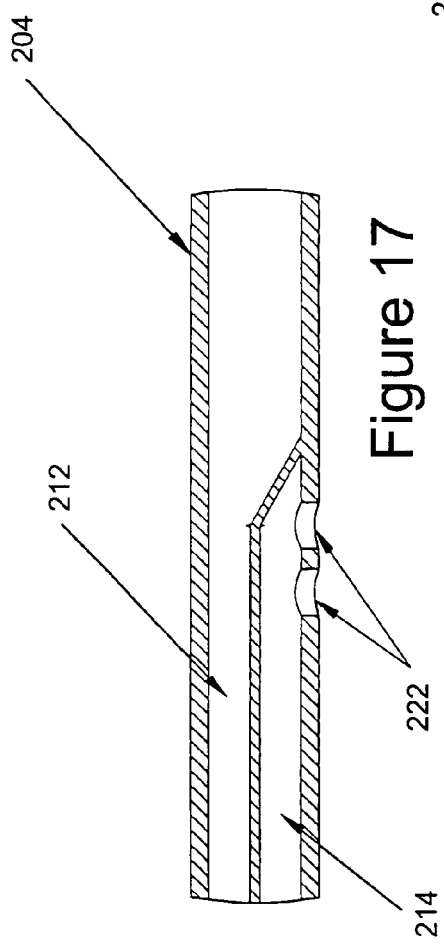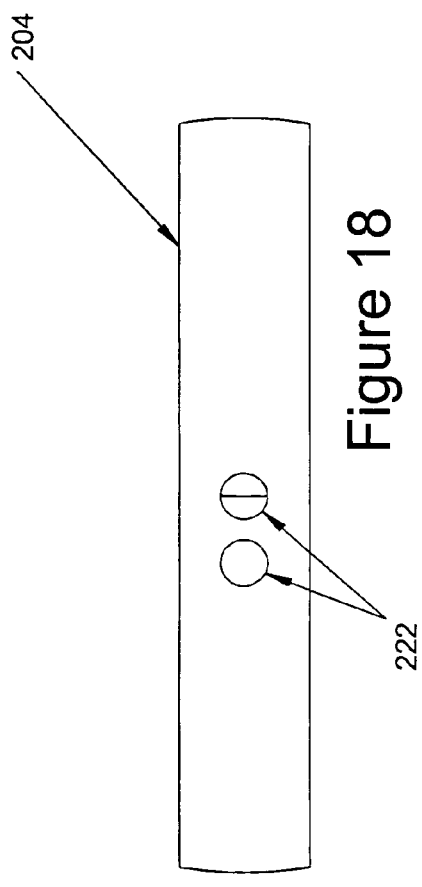

Figure 28

| At Qb=40ml/m, Quf=100 ml/hr | |
|---|---|
| Recirculation % | % Hct Increase |
| 5 | 0.1 |
| 10 | 0.5 |
| 20 | 1.1 |
| 30 | 1.9 |
| 40 | 3 |

Figure 29

| At Qb=40ml/m, Quf=500 ml/hr | |
|---|---|
| Recirculation % | % Hct Increase |
| 5 | 1 |
| 10 | 3 |
| 20 | 7 |
| 30 | 13 |
| 40 | 21 |

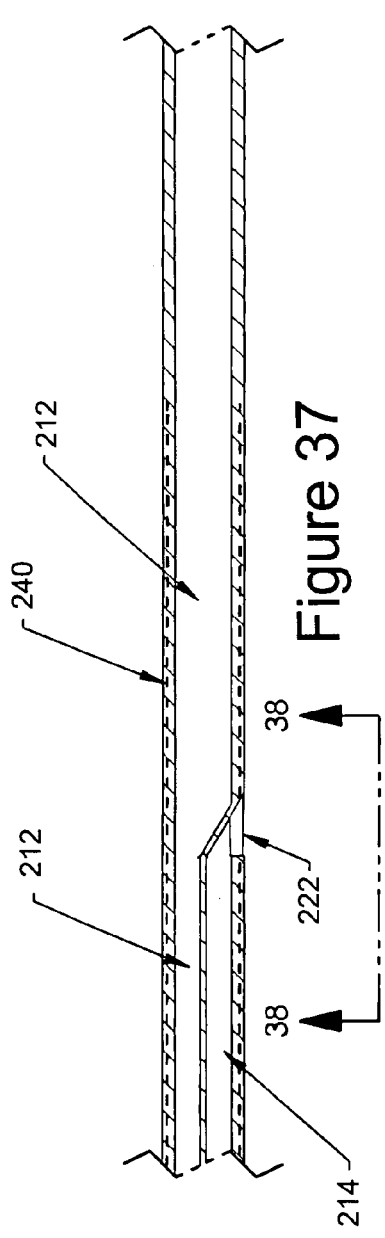
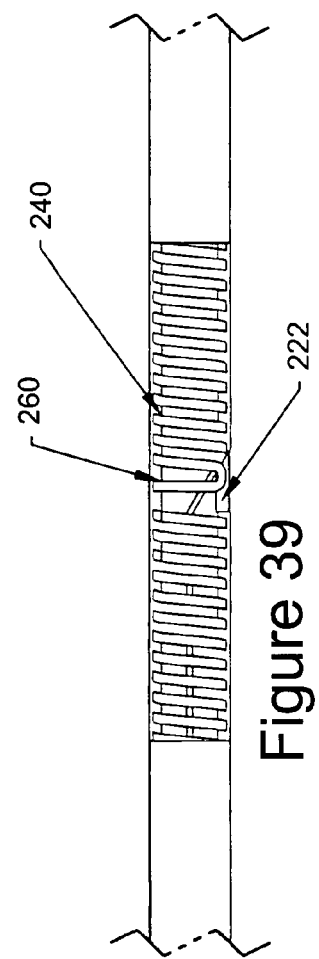
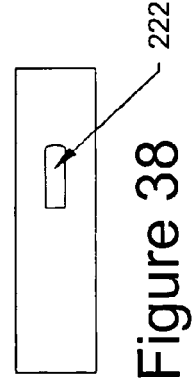
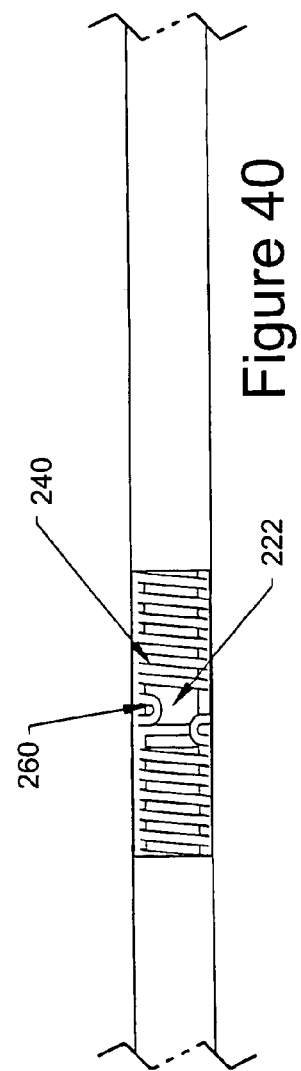

METHOD AND APPARATUS FOR ULTRAFILTRATION UTILIZING A PERIPHERAL ACCESS DUAL LUMEN VENOUS CANNULA

FIELD OF THE INVENTION

This invention relates to the extracorporeal treatment of blood and more particularly to the blood access for Renal Replacement Therapy and treatments using an artificial kidney. It is also related to the treatment of congestive heart failure and fluid overload in a patient.

BACKGROUND OF THE INVENTION

Renal Replacement Therapy (RRT) is a class of medical treatments that artificially provides functions that would naturally be provided by the kidneys. RRT performs two primary functions: (i) ultrafiltration (removal of water from blood plasma), and (ii) solute clearance (removal of different molecular weight substances from blood plasma). Mechanical RRT generally involves an extracorporeal blood circuit that treats blood that is temporarily removed from and then returned to a patient. Devices used for RRT generally include: an extracorporeal blood circuit that extends from the patient through a filter and back to the patient; a pump acting on the blood circuit tube that moves the blood through the tube and filter; a filter where the blood components are separated and where the solute exchange takes place; and blood access devices. In addition, a mechanical RRT device may include a controller to regulate the pump(s), which in turn control the flow rate of blood and other fluids through the circuit, and detect blockages and leaks in the blood circuit.

In operation, blood from a patient flows through the RRT blood circuit at a flow rate determined by the blood pump speed. As the blood flows through the filter, certain fluids, solutes or both from the blood pass through the filter membrane and are extracted from the blood plasma. The extracted fluids with solutes flow from the filter through a filtrate tube and are temporarily stored in a filtrate bag. The extraction of fluids and/or solutes by the RRT device replaces or supplements the natural functions of the kidneys. Fluids may be injected into the remaining blood plasma which then flows through the blood circuit tube and is infused into the patient.

The filter in an RRT device, also called hemofilter or "dialyzer", can be set up to perform fluid removal, solute clearance, or both. The RRT device may also operate with or without fluid replacement. "Clearance" and "ultrafiltration" are common terms used in RRT. "Clearance" is the term used to describe the net removal of substances, both normal and waste product, from the blood. "Ultrafiltration" is the term used to describe the removal from the blood plasma of plasma water, without significant affect on the concentration of small solutes in the blood plasma. In mechanical terms "Ultrafiltration" is the convective transfer of fluid out of the plasma compartment of a filter through pores in the filter membrane and into a filtrate output compartment of the filter.

Blood filters generally have a blood compartment within input and output ports connected to the blood circuit, a filter membrane, and a filtrate compartment. The membrane separates the blood compartment and the filtrate compartment in the filter. In a filter used primarily for ultrafiltration, the pores of the filter membrane may be hollow fibers having blood passages of approximately 0.2 mm or less in diameter. The filter membrane pass fluids, electrolytes and small and middle sized molecules (typically up to 50,000 Daltons) from the blood plasma. The ultrafiltrate output from the filtration pores is similar to plasma, but without the plasma proteins or blood cells. In an ultrafiltration filter, the concentration of small solutes is the same in the ultrafiltrate as in the plasma, and no clearance or concentration change is obtained of small solutes in the blood plasma that is returned to the patient. However, the ultrafiltration does remove water from the blood and is useful for treating patients suffering from fluid overload. During the ultrafiltration treatment of a fluid overloaded patient the fluid that is mechanically "filtered" or removed from blood is typically immediately replaced by the access fluid that has been stored in the body. As a result the excess fluid or "edema" in the legs, the abdomen and the lungs of the patient is reduced and the patient's condition is relieved.

Dialysis is a different form of RRT. Dialysis is the transfer of small solutes out of a blood plasma compartment of a filter by diffusion across the filter membrane. Dialysis occurs as a result of a concentration gradient across the filter membrane. Diffusion of small solutes occurs from the filter compartment with a higher concentration (typically the blood compartment) to a compartment with lower concentration (typically the dialysate compartment). Since the concentration of solutes in the plasma decreases, clearance is obtained. Fluid removal does not necessarily occur during dialysis.

Ultrafiltration can be combined with dialysis to remove both fluid and small solutes from the blood plasma during RRT. Hemofiltration is the combination of ultrafiltration and fluid replacement. The volume of the replacement fluid is typically much larger than is needed just for fluid control. The replacement fluid generally contains electrolytes, but not other small molecules. There is some clearance because there is a net removal of small solutes due to both replacing fluids without small solutes and ultrafiltration of fluid with small solutes. A primary difference between the ultrafiltration and hemofiltration treatments is that during the former the plasma water removed from blood is replaced by the natural excess fluid internally stored in the patient's body. During the later the replacement solution is supplied by the treatment in a form of an artificial infusion.

Generally, all modes of Renal Replacement Therapy involve the removal of blood (typically venous) from a patient and passing the blood through a hollow fiber filter where there occurs fluid removal and, if desired, a solute removal or exchange. After passing through the filter, the blood is returned to the blood stream of the patient. So-called "batch" type RRT devices extract and return blood through the same single lumen IV catheter or "needle" and blood tube by reversing the direction of the blood pump. More common "continuous" type devices extract and return blood continuously using one double lumen catheter in the same vein or separate catheters in two separate veins. Catheter and needles used in RRT are generally known as "blood access". Some RRT patients have permanently lost their kidney function and need to undergo dialysis several times a week. These patients typically have surgically implanted or modified sites for blood access such as arterial-venous shunts or fistulas.

Congestive Heart Failure (CHF) patients can benefit from fluid removal by ultrafiltration of blood. CHF patients have functional kidneys, but suffer from fluid overload due to CHF. The kidneys of CHF patients are generally healthy but are not fully functioning due to the failing heart and low blood pressure. Because the kidneys are not fully functioning, fluids build up in the patient and the fluid overload contributes to the stress on the already failing heart. The kidneys do produce urine that is usually sufficient for the kidneys to remove toxic solutes.

CHF patients need an RRT treatment that removes excess fluid from the body. These patients typically do not require solute removal or a long-term chronic treatment as in the chronic dialysis patient. The fluid can be removed from the patient relatively quickly and the treatment stopped. The reduction of fluid overload should relieve the stress on the heart sufficiently so that the heart is able to resume adequate perfusion of the kidney. Even if the heart is unable to adequately perfuse the kidney after the fluid overload treatment, the patient often enjoys several days or weeks before the fluid overload condition again becomes sufficiently severe to undergo another ultrafiltration treatment. These CHF patients need a RRT treatment that is simple to establish and safe.

Fluid overload can lead to several painful and dangerous conditions, including excessive fluids in the lungs. If excessive fluid in the lungs is not promptly removed with a diuretic medication, CHF patients are often intubated and placed on a ventilator. If the initial diuretic therapy has little affect, more aggressive treatment with increasingly potent diuretics is needed. In addition, inotropic agents such as dobutamine are administered to increase the pumping function of the heart and raise the blood pressure. Higher blood pressure is expected to assist in the perfusion of the kidneys and make diuretics work. In more recent years, vasodilator therapy became a part of the standard therapy for a severely volume-overloaded, decompensated CHF patient. All the above-mentioned therapies as a rule require admission to an intensive care unit (ICU) of a hospital. Potentially dangerous side affects of drugs and the need for advanced monitoring and intubation are the main reasons for a typical ICU admission. ICU admissions are expensive and require specialized doctor and nurse caregivers.

Previously, standard drug therapy was frequently unable to remove excess fluid rapidly enough to prevent hospitalization. There is a clear and unmet clinical need for a CHF treatment that allows physicians to rapidly, controllably and safely remove a clinically significant amount of fluid from a CHF patient. Such a treatment would potentially reduce the need for excessive hospital admissions and decrease the duration of hospital stays.

Ultrafiltration (one mode of Renal Replacement Therapy) is useful for removal of excess fluid from a patient, especially in CHF patients whose kidneys are not working but are generally healthy. Ultrafiltration has not been used widely in the treatment of patients with CHF, despite its clinical benefits for treating fluid overload. There are several issues that have in the past limited the use of currently available ultrafiltration devices. One of these factors is that prior ultrafiltration devices draw large volumes of blood out of the body and, thus, require so called central venous access. Central venous access implies that a relatively large diameter catheter is placed with its tip in a major vein in the "center" of the patient's body. Typically the central catheter is placed in the superior vena cava or right atrium of the heart of the patient. This procedure requires specialized skill and is also associated with serious complications such as bleeding, perforated lung or heart and infections. As a result, mechanical fluid removal in CHF patients has in the past been performed in the ICU of a hospital where resources, training and adequate nursing monitoring are available.

With the increasing prevalence of decompensated CHF and the increased cost of hospital admission and even more so of an ICU treatment, a strong need has emerged for a new technology that will allow fluid removal in the non critical care setting. This need is for a device and technique that is simple and safe so that it could be used in the outpatient setting, doctor's offices, Emergency Rooms (ER) and general hospital floors. Such treatment would be acceptable if access to venous blood was established via a peripheral vein in the patient's arm or other peripheral vascular site on the patient. An advantage of accessing blood through a peripheral vein in the arm is well recognized. Unlike the central veins, the peripheral veins are close to skin and easier to identify. Physicians and nurses are trained to place needles and catheters in the peripheral veins of an arm. Venopunctures are easy to monitor for infiltration of fluid and thrombosis and the control of infection is simpler than with central catheters. Also, the potential loss of a peripheral vein to thrombosis is less critical.

SUMMARY OF THE INVENTION

An ultrafiltration technique has been invented that relies on peripheral vein access. This ultrafiltration technique is described in commonly-owned U.S. Pat. No. 6,533,747 entitled "Extracorporeal Circuit for Peripheral Vein Fluid Removal", the entirety of which is incorporated by reference, and in U.S. Pat. No. 6,890,315 (now pending U.S. patent application Ser. No. 09/618,759, filed Jul. 18, 2000, entitled "Method and Apparatus for Peripheral Vein Fluid Removal in Heart Failure", the entirety of which is incorporated by reference. The volume of blood that can be drawn from a peripheral vein is substantially less than can be drawn from a central access vein. Nevertheless, the relatively-small volume of blood removed from peripheral veins has been found sufficient for ultrafiltration for most CHF patients suffering from fluid overload.

Clinical trials of ultrafiltration in CHF patients have been performed using standard and novel devices for peripheral access to blood. Ultrafiltration using peripheral vein access with standard needles or catheters has recently successfully treated several CHF patients. However, standard peripheral vein access has not been successful for all CHF patients. The peripheral vein access had been performed using conventional short (3–4 cm long) catheters inserted into a peripheral vein in the arm of the patient. The peripheral veins in some CHF patients have such poor blood flow that the veins collapse around the area of the catheter tip when short peripheral catheters were used to continuously draw blood for ultrafiltration. Some CHF patients also have as few as one peripheral vein sufficient for venous access. Typically this is due to bloating of the extremities caused by fluid overload, repeated needle sticks from previous venous access procedures, and other venous complications present in many aging CHF patients. For these patients, conventional access devices are not sufficient for ultrafiltration. These CHF patients require some other blood access mechanism to remove fluids from their blood stream and provide relief from fluid overload.

Single site peripheral venous access through a dual lumen catheter is preferred as opposed to multiple vein punctures for the withdrawal and return of blood. This would minimize preparation time, vessel trauma and help conserve veins for future vascular interventions.

There is a need for a simplified removal of excess fluid from fluid overloaded patients having poor blood flow in their peripheral veins and limited peripheral access sites that is inexpensive, relatively easy to apply and does not require a hospital ICU. Devices and methods have been developed and are disclosed here to remove excess fluids through extended length blood access catheters introduced via a peripheral vein, for example, in the patient's arm. These devices and methods safely continuously withdraw and return blood from a peripheral vein at substantially higher flow rates than the peripheral vein would normally permit. The volume of blood withdrawn from the venous system of a patient through a catheter inserted into a peripheral vein is sufficient for ultrafiltration and fluid overload relief, even for those patients having poor blood flow in their peripheral veins. These devices and methods are safer and simpler than the traditional central vein access catheters.

In forty percent (40%) to eighty percent (80%) of relatively young and healthy people with good veins, continuous blood flow of 40 to 120 mL/min (milliliters per minute) can be established via standard short length (3–4 cm) peripheral vein access needles or catheters. Peripheral veins in the arm such as basilic, cephalic or antibrachial vein are often used to infuse medication or to draw blood from a patient. Patients are commonly asked to increase their blood supply to the arm by squeezing a rubber ball to improve the blood withdrawal. This method using short length catheters is commonly used in extracorporeal blood treatment procedures such as aphaeresis. When patients and blood donors do not have appropriately large veins, they are usually not accepted for treatment. Where the treatment is lifesaving, such as in chemotherapy for blood cancer, central line catheters are placed to allow access to blood.

Based on clinical studies, peripheral vein access using short length catheters has had limited success for blood withdrawal to perform fluid removal in chronically ill CHF patients. Many CHF patients have poor blood flow through their peripheral veins. Effective fluid removal treatment for CHF patients generally requires fluid removal rate of 250 to 1000 mL/Hour. It has been discovered that the 500 mL/Hour fluid removal rate is preferred by physicians in CHF patients.

It is not practical to extract more than 20% to 30% of volume of blood as ultrafiltrate. This implies that to remove 500 mL/Hour (8.3 mL/min) of fluid from the patient, continuous blood flow of at least 40 mL/min through the filter is desired. Attaining this rate in many CHF patients can be difficult. CHF patients are typically elderly. The surface veins in the arms of many CHF patients have been punctured many times during prior medical treatments, and the veins often have stenosis. Moreover, as a result of heart failure, these patients have reduced cardiac output (i.e., total amount of blood pumped by the heart). In response to their poor cardiac output, the circulatory system of these patients reduces the blood supply to peripheral organs (including the arms and the hands), in order to maintain an adequate blood supply to the brain, heart and other vital organs.

Applicants determined that the difficulties with withdrawing and returning blood at rates of 40 to 60 mL/min were due primarily to three conditions:

(a) Intermittent collapse of the peripheral vein around the tip of the withdrawal catheter needle. The vein collapse appears to have been due (at least in part) to the small caliber of the surface peripheral veins used for withdrawal and low venous pressure in the vein. Suction of blood at the tip of the catheter generated a negative pressure zone in the blood and caused intermittent vein collapse. The collapse of the vein prevents withdrawal of blood until the vein returned to its original shape. This first condition could be compensated for in some CHF patients by straightening or relaxing the arm of the patient.

(b) Flow demand determined by the pump in the ultrafiltration device exceeded the blood supply available to the peripheral vein being used for withdrawal. Because the pump demanded a flow of blood more than was available in the peripheral vein, a negative pressure resulted that collapsed the vein. While the pump controller had automatic feedback that reduced the pump speed when the pressure in the withdrawal tube began to drop, the feedback controller could not adequately compensate for the inadequate blood flow through the peripheral vein in some CHF patients.

(c) Inability to gain separate access sites for both withdrawal and return of blood. Typically this is due to bloating of the extremities caused by fluid overload, repeated needle sticks from previous venous access procedures, and other venous complications present in many aging CHF patients.

Based on experiments, it was concluded that a fundamental problem of blood withdrawal from a peripheral vein is the dependence on the drainage from the arm and the hand for blood supply. The available blood flow for withdrawal in a surface peripheral vein is limited to the blood draining from the capillary system. If the blood draining from the capillary system is not sufficient for ultrafiltration treatment, then using conventional local peripheral vein access to withdraw blood becomes unworkable. This problem of inadequate drainage of blood from the capillary system is greatly exacerbated in CHF patients where the arterial blood supply to the arm is reduced compared to healthy subjects.

A solution to inadequate blood flow for withdrawal from peripheral veins is to withdraw blood from other regions of the circulatory system that have a generous supply of blood flow. For example, central catheters draw blood from the large pool of venous blood in the right atrium or the adjacent vena cava. Venous blood collected in these "great vessels" is the combined drainage from all body organs. Even in a CHF patient with reduced cardiac output it is never less than 3 to 4 L/min. The caliber of these central vessels is large compared to the size of the catheter and continuous withdrawal of as much as 200 to 400 mL/in is possible, even for CHF patients.

Central venous catheters have been used to perform Renal Replacement Therapy and fluid removal in CHF patients. However, central venous catheters are difficult to insert into a patient, require surgery and fluoroscopy to be inserted and removed and generally are closely monitored while a patient is in an ICU during the entire ultrafiltration treatment. Moreover, the risk associated with the placement of central venous catheters limit their use to critically ill patients. Central venous catheters are generally inserted as a life saving measure to relieve critically dangerous fluid overload conditions in CHF patients in danger of imminent death.

Theoretically, all veins in the human body are connected. The network of veins in a human body include a trunk vessel (central venous cavity) connected to the right atrium of the heart. From the central venous cavity extends many branches of veins that each branch progressively to smaller and smaller veins until the veins become tiny capillaries that connect to the arterial circulatory system. In the venous system, blood drains from the capillaries and flows to the progressively larger veins until all veins drain into the large flow of the central venous cavity. Thus, the largest supply of blood in the venous system is downstream of the blood flow, which is ultimately the central venous cavity. In contrast, the largest supply of blood in the arterial system is upstream because blood flows from the central arteries and downstream towards the capillaries.

In the venous system, it would be useful to draw blood from the downstream sources of venous blood. However, to draw blood from downstream of the peripheral vein from the location near the insertion point of a catheter would require that blood flow backward from the central venous pool through the network of branching vessels into the catheter. Drawing venous blood from downstream in a vein is a technique known as retrograde (opposite to the natural direction) flow. In contrast to retrograde flow, antegrade flow is the withdrawal of blood in the same direction as the natural flow of blood.

Retrograde blood withdrawal from the peripheral vein in an arm (or other body extremity) where these veins come to the body surface and where the traditional catheters are inserted is almost impossible because the peripheral veins in arms and legs prevent retrograde flow and do not allow for blood to flow upstream to a catheter tip intake opening. Peripheral veins have a series of one-way valves (venous flapper valves) along their path. These one-way valves prevent retrograde flow, and prevent venous blood from the central venous cavity flowing upstream through the vein towards the catheter tip. The valves are spaced along the length of the peripheral vessels. The valves are constructed of flappers or leaves that can be bent easily in the downstream direction to permit the downstream flow of blood. The flappers shut closed if the flow of blood reverses and this closure prevents the upstream (retrograde) flow of blood through peripheral veins.

The natural purpose of venous flapper valves is to prevent retrograde blood flow when a person moves and thereby applies inertia and centrifugal forces to the blood in the veins. The valves also prevent pooling of blood at the lower extremities, e.g., hands and feet, due to the force of gravity. In patients that have defective "incompetent" venous valves, it is common to see bulging distended veins in the legs. These venous valves, which appear to work quite well in some CHF patients, prevent retrograde flow of blood to a short peripheral catheter inserted into the arm of a CHF patient. It is believed that the venous flappers are a principal reason why retrograde flow is prevented when a peripheral catheter applies a local negative pressure in a peripheral vein. Accordingly, there is a need to overcome or circumvent the natural venous flappers. By circumventing these flappers, a peripherally inserted catheter should be able to create a sufficient negative pressure to cause retrograde blood flow and, thus, increase the blood flow through a catheter for ultrafiltration treatment without collapsing the vein. A single lumen long peripherally inserter catheter for ultrafiltration is disclosed in commonly-owned U.S. patent application Ser. No. 2002/0,187,069 entitled "Method And Apparatus For Ultrafiltration Utilizing A Long Peripheral Access Venous Cannula For Blood Withdrawal" and published Dec. 12, 2002. However, a single lumen catheter approach requires a skin access site for the withdrawal catheter and a second access site for the infusion catheter. Moreover, a single long lumen withdrawal catheter relies on natural blood pressure to provide sufficient blood flow through the portion of the peripheral vein along the length of the catheter. If the natural blood pressure is too low in the peripheral vein, then there may be insufficient blood flow in the portion of the peripheral vein along the length of the catheter.

A solution set forth herein to overcome limited access sites and potential for inadequate blood flow along the catheter length is to withdraw and return blood from a single site using a dual lumen catheter and to provide an infusion discharge port in the catheter near the access site. One skin access site is preferred for most patients because it requires only one vein puncture for the patient. Each puncture creates scar tissue after a catheter is removed and the vessel heals. As a patient gets older and receives additional intravenous and interventional vein therapies these areas of scar tissue accumulate and eventually become the limiting factor in the physician's ability to treat the patient percutaneously. Providing the infusion discharge port near the access site provides additional blood flow to the section of the peripheral vein that contains the catheter. Blood infused from the catheter enters the peripheral vein, mixes with blood already in the vein and flows in the vein along the length of the catheter.

To avoid special nurse training for catheter insertion and to minimize the risk of patient complications such as vein thrombosis, vessel perforation, and patient discomfort the catheter outside diameter may be 6F or less. Larger catheters are generally not practical for routine peripheral access as they can significantly obstruct blood flow through a peripheral vein and are not routinely inserted by nurses or I.V. teams. The use of conventional catheter designs in conjunction with these two constraints of length and diameter results in withdrawal and return pressures that are well beyond the desired limits for a continuous extracorporeal blood control system of ±300 mmHg. This is due to the high resistance to flow created by the locations and relatively small cross sectional areas of the withdrawal and infusion lumens at lengths of at least 20 cm long and outside diameter of 6F or less.

Conventional multi-lumen central venous catheters for continuous withdrawal and return of blood utilize the proximal lumen for withdrawal and the distal lumen for return. The primary reason for this is to prevent re-circulation such as in dialysis. Significant effort has been directed into dialysis catheter designs to minimize the level of recirculation. Access recirculation reduces dialysis adequacy by reducing the urea concentration entering the dialyzer. As a result the patient is subjected to extended dialysis sessions or to clinical complications associated with inadequate dialysis. Recirculation studies with well functioning catheters (blood flow of at least 300 ml/min) have shown the mean dialysis urea reduction ratio to be significantly higher for catheters having an average 4.1% recirculation than for catheters having an average 16.1% recirculation. (Leblanc M, Fedak S, Mokris G, Paganini E P: Blood recirculation in temporary central catheters for acute hemodialysis. Clin Nephrol. 1996 May; 45(5):315–9.) Based on National Kidney Foundation DOQI (Dialysis Outcomes Quality Initiative) guidelines, dialysis access recirculation exceeding 5–10% should prompt investigation of its cause.

A solution to these shortcomings of existing dual lumen catheters has been discovered by the applicants. The design disclosed herein results in a 6F dual lumen catheter at least 20 cm long that uses its distal end for blood withdrawal and a shorter second lumen for blood return whose length is no more than 10 cm long. By withdrawing blood from its distal end, the catheter is able to draw from a large pool of blood by accessing the retrograde blood supply as described above. The invention produces acceptable dual lumen system operational pressures by optimizing the cross sectional areas of the internal flow lumens throughout the catheter length. This is accomplished by keeping the outside diameter of the catheter substantially equivalent throughout its length and by expanding the cross sectional area of the withdrawal lumen in the distal length of the catheter after the end of the return lumen.

The constraints associated with dual lumen peripheral access limit the maximum withdrawal flow rate of blood to 40–60 ml/min or less in patients with hematocrit no greater than 50%. Blood flow rates of between 10 and 40 ml/min enable fluid removal rates of between 125 and 500 ml/min. The lower removal rates are clinically accepted based on the increased ease of use with a single stick dual lumen catheter system. These lower removal rates are also more desirable in hemodynamically unstable patients as well as those requiring lower "maintenance" removal rates such as in an out-patient setting.

The reversal of the withdrawal and return lumen locations does not create a significant amount of recirculation. Adequate ultrafiltration therapy can be delivered in the presence of up to 33% recirculation. Recirculation is of concern during ultrafiltration if it increases the blood Hct to above a level at which ultrafiltration cannot be performed and results in the filter clotting. A good rule of thumb is to allow a maximum of 15% increase in Hct. Thus, if the patients base Hct was 40% a withdrawal Hct of greater than 46% would be considered excessive due to blood recirculation.

The inventive devices and methods disclosed here provide a means for relieving fluid overload in CHF patients who cannot be successfully treated with the conventional peripheral vein blood withdrawal but in whom the placement of central catheters is not desired or justified. The devices and methods developed by applicants combine the access to a large pool of blood (an advantage of central catheters) with the ease and safety of dual lumen peripheral vein access. By combining the advantages of central catheter access and dual lumen peripheral vein access, the present invention provides a technique for providing ultrafiltration (or other RRT treatment such as slow continuous hemofiltration at modest replacement rates) outside of the ICU environment for those patients that have inadequate blood flow in their peripheral veins as well as limited venous access sites.

BRIEF DESCRIPTION OF THE DRAWINGS

A best mode embodiment(s) of the invention is illustrated in the attached drawings that are described as follows:

FIG. 5 is a perspective view of a first embodiment of a dual lumen peripheral catheter.

FIG. 6 is an enlarged view of region 6 marked in FIG. 5 of the distal opening of the infusion lumen of the dual lumen peripheral catheter.

FIG. 7 is an enlarged view of region 7 marked in FIG. 5 of the distal opening of the withdrawal lumen of the dual lumen peripheral catheter.

FIG. 8 is a cross-sectional view of a longitudinal section view of the dual lumen peripheral catheter shown in FIG. 5, where the view is taken along line 8—8 in FIG. 9.

FIG. 9 is an end view of the dual lumen peripheral catheter shown in FIG. 5.

FIG. 10 is a cross-sectional view of an enlarged longitudinal section view of the hub region of the dual lumen peripheral catheter as marked by region 10 in FIG. 8.

FIG. 11 is a cross-sectional view of an enlarged longitudinal section view of the distal opening area of the infusion lumen of the dual lumen peripheral catheter as marked by region 11 in FIG. 8.

FIG. 12 is a cross-sectional view of an enlarged longitudinal section view of the distal opening area of the withdrawal lumen of the dual lumen peripheral catheter as marked by region 12 in FIG. 8.

FIG. 13 is a side view of the dual lumen peripheral catheter shown in FIG. 5.

FIG. 14 is a catheter cross-sectional view taken along line 14—14 in FIG. 13 to show the proximal dual lumen section of the dual lumen peripheral catheter.

FIG. 15 is a catheter cross-sectional view taken along line 15—15 of FIG. 13 and shows a transition region between the dual lumen section and a single lumen section of the dual lumen peripheral catheter.

FIG. 16 is a catheter cross-sectional view taken along line 16—16 of FIG. 13 and shows a section view of the distal withdrawal single lumen region of the dual lumen peripheral catheter.

FIG. 17 is a cross-sectional view of the transition region and another embodiment of the distal opening region of the infusion lumen of a dual-lumen peripheral catheter, wherein the opening region has a two-hole configuration for the infusion lumen distal opening.

FIG. 18 is a side view of the two-holes of the infusion lumen shown in FIG. 17.

FIG. 19 is a cross-sectional view of a distal opening region of the infusion lumen of a dual-lumen peripheral catheter, wherein the opening region has a two-hole configuration for the infusion lumen distal opening and the two-holes are angled with respect to the axis of the lumen.

FIG. 20 is a side view of the angled two-holes of the infusion lumen shown in FIG. 19.

FIG. 28 is a chart of the effect that various recirculation rates have on the withdrawal line blood hematocrit at a blood flow rate of 40 ml/min and an ultrafiltration rate of 100 ml/hr.

FIG. 29 is a chart of the effect that various recirculation rates have on the withdrawal line blood hematocrit at a blood flow rate of 40 ml/min and an ultrafiltration rate of 500 ml/hr.

FIG. 37 is a cross-sectional view taken longitudinally along an axial length of a fourth embodiment of a dual lumen catheter having an embedded stiffener in the catheter wall.

FIG. 38 is a side view of a portion of the fourth catheter embodiment showing a discharge opening for the infusion lumen.

FIGS. 39 and 40 are side views of a portion of the fourth catheter embodiment showing the stiffener in a cut-away section of the catheter wall.

DETAILED DESCRIPTION OF THE INVENTION

Figure 1:
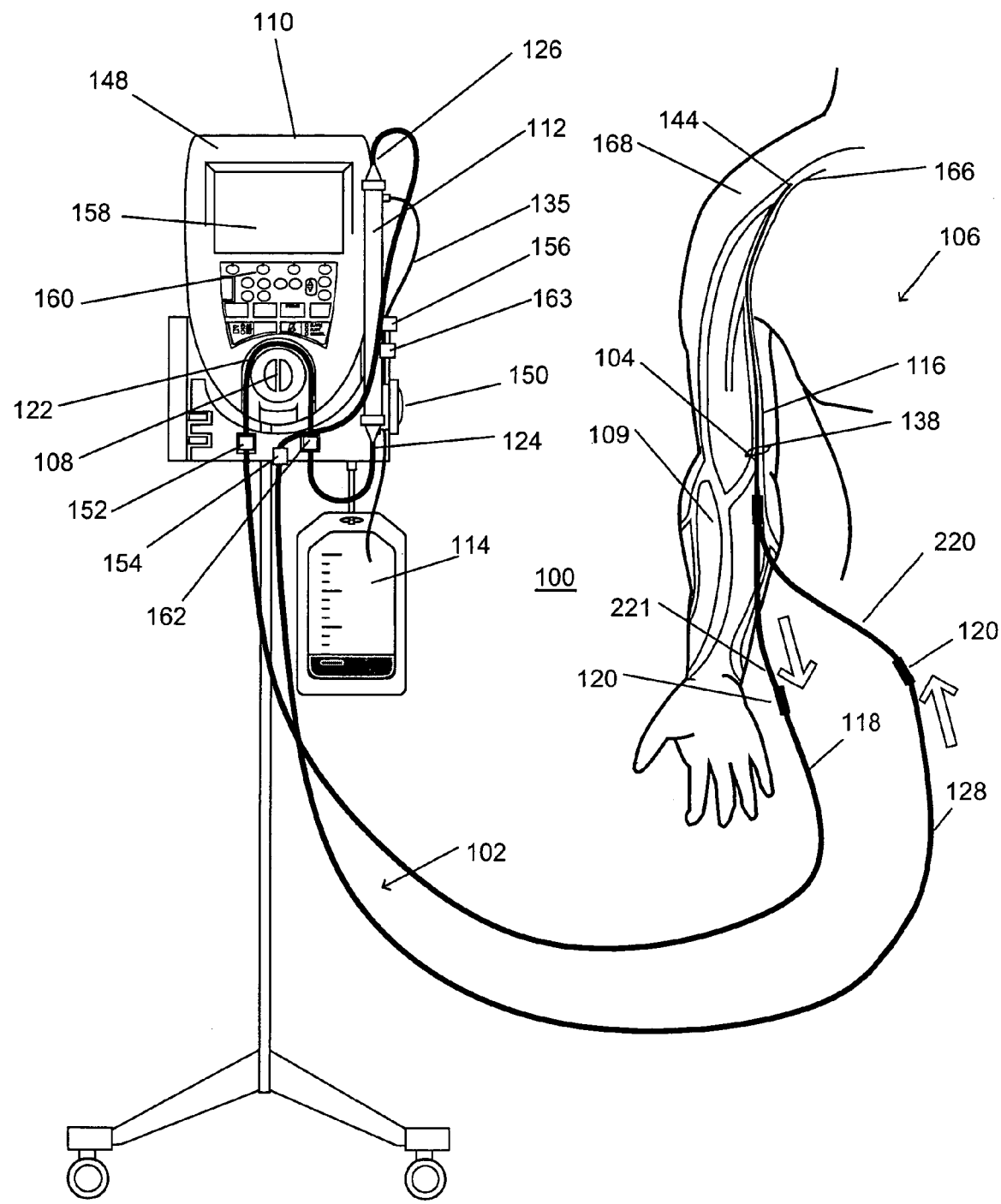
FIG. 1 illustrates an intravenous blood ultrafiltration system using a dual lumen middle length peripheral access venous blood catheter.

FIG. 1 shows an intravenous blood ultrafiltration system 100 having an extracorporeal blood circuit 102 that includes a dual lumen middle length peripheral access venous blood cannula 104, commonly called a Peripherally Inserted Central Catheter (PICC). The disclosed blood circuit is a single use disposable set for ultrafiltration of blood to treat fluid-overload in patients 106. The ultrafiltration system and blood circuit are intended to be used in a non-ICU setting and to not require surgery.

Effective treatment of fluid overload by ultrafiltration of blood with a dual lumen catheter generally requires at least 10 to 40 mL/min of withdrawn blood. The rate of blood flow required for ultrafiltration could consume substantially all of the blood flowing through the peripheral veins of many CHF patients. However, only a portion of the blood flowing through the peripheral vein may be withdrawn. During blood withdrawal, the resistance of interconnecting branches of the venous tree in the patient's arm 109 slows the refilling of a specific vein segment and further reduces the rate of blood flowing through the peripheral vein and available for peripheral withdrawal.

Figure 2:
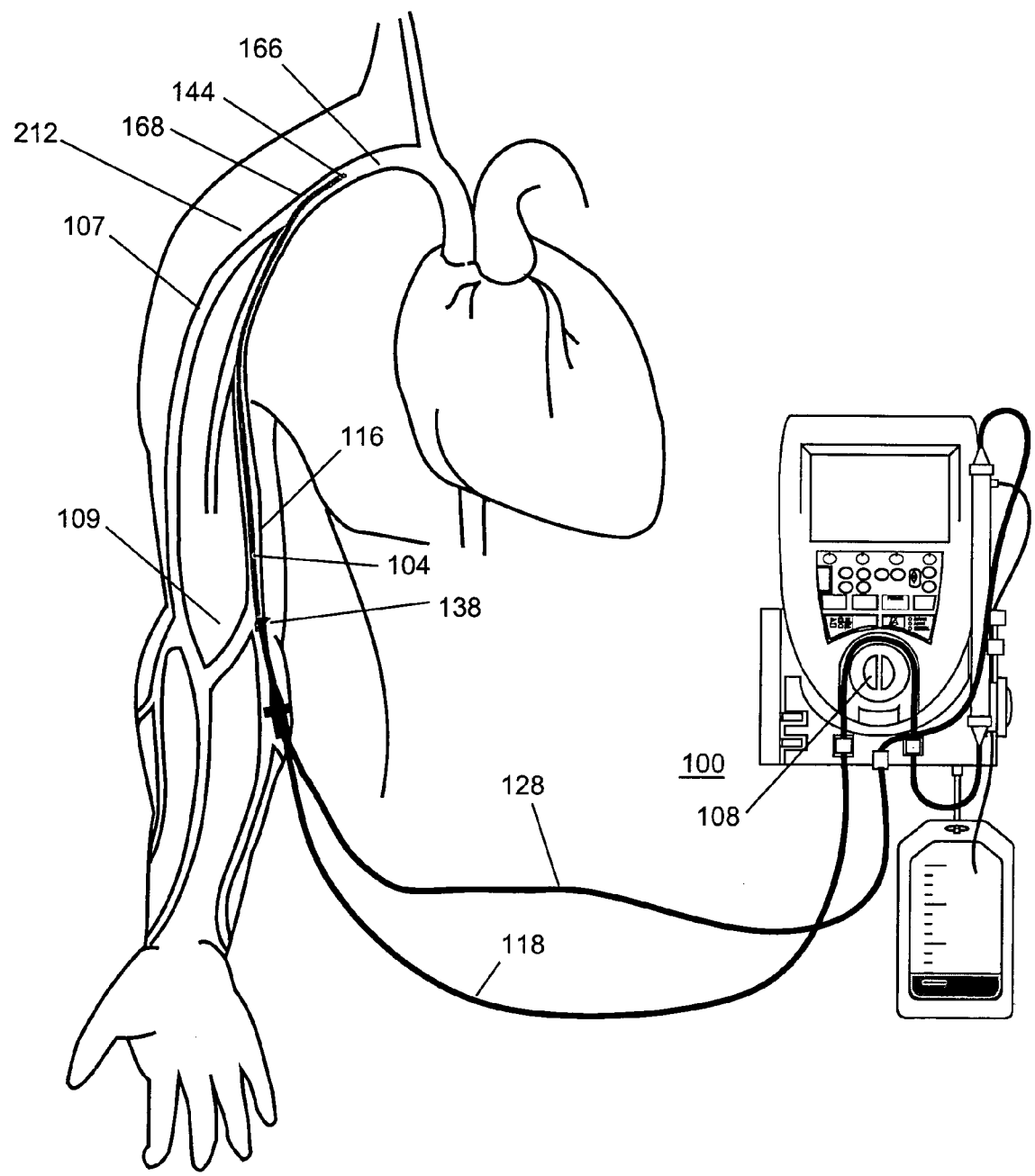
FIG. 2 illustrates a placement of the dual lumen middle length peripheral access venous blood catheter in the patient.

With reference to FIG. 2, the maximum flow rate of venous blood that can be withdrawn from the peripheral vein 116 (such as in the arm 109 of the patient) in the proximity to the catheter insertion location 138 is the rate of blood that returns (drains) from the network of skin and muscle blood capillaries. These capillaries are supplied by oxygen rich arterial blood coming from the left ventricle of the heart. Moreover, the total venous drainage from an organ cannot exceed the arterial blood supply to the organ. An arm and a hand in a healthy person at rest have a blood supply rate of approximately 100 to 260 mL/min of blood. This rate can vary with the hand temperature. In a heart failure patient the flow rate in the arm and hand can be reduced by 20% to 40% below the rate of a healthy person. Accordingly, the flow rate of blood through a peripheral vein in a CHF patient may be only 60 to 208 mL/min.

In addition, the caliber of peripheral veins 116 in the arm in a person can be 2 to 3 mm. A metal or plastic 16 to 20 Gage phlebotomy needle is commonly used to draw blood for various clinical needs. A standard catheter needle for a peripheral vein phlebotomy can be 25 to 45 mm long. If a 16 Gage needle (approximately 1.65 mm outer diameter) is placed in such a vein it will almost occlude the vein and will be prone to collapse the walls of the vein around it with the application of negative pressure. Also, blood vessels in an arm tend to vasoconstrict (contract) in response to neurological and hormonal stimuli. The patient's motion can intermittently cut off the blood supply.

For effective ultrafiltration treatment to relieve fluid overload with a dual lumen access catheter, blood should be removed from a CHF patient at a rate of 10 to 40 mL/min. At these rates, four (4) to twelve (12) hours of peripheral vein access ultrafiltration will result in the removal of one half (0.5) to six liters (6) of filtrate fluid from the blood. Generally, 2 to 4 liters of fluids are removed to relieve a CHF patient suffering fluid overload. A treatment time of 4 to 12 hours is relatively long and often there is a strong desire to complete the treatment in a period closer to 4 hours. Increasing the blood withdrawal flow rate is a key to minimizing the ultrafiltration treatment time. It has been difficult to increase the withdrawal flow rate, especially in those CHF patients having low blood flow through their peripheral veins. Conventional techniques for increasing blood flow are not practical. For example, it is not practical to expect that a heart failure patient in a severe fluid overload condition will squeeze a rubber ball in his hand to improve blood flow to the arm for 4 to 12 hours. Accordingly, there is a need for devices and techniques to withdraw blood from peripheral veins at substantially higher rates than have in the past been obtainable.

In view of the limitations described above, fluid removal in volume overloaded CHF patients via a peripheral vein using standard-length phlebotomy needles has been impractical for many CHF patients. Experiments have been conducted for blood withdrawal and infusion using 20 Gage, 18 Gage and 16 Gage plastic needles 35 to 40 mm long inserted in lateral antibrachial, cephalic, basilic and other adjacent surface veins at the arm bend at the elbow of patients. These patients varied widely in body size, age and medical condition. The objective of the experiment was to withdraw blood continuously using a computer controlled roller pump at 40 to 60 mL/min. Blood was continuously re-infused into a different vein in the opposite arm of the patient. During the experiment, treatment time ranged from 15 minutes to 4 hours. Infusion of 40 to 60 mL/min of blood into almost any vein in the arm or hand of CHF patients was always possible. However, withdrawal of blood from peripheral veins at the same rates of 40 to 60 mL/min was problematic in as many as 50% of CHF patients and impossible in as many as 20% of these patients.

Blood can be withdrawn from a large volume 166 of venous blood that is upstream of the peripheral veins at the large and great veins of the vascular system. A wide variety of Peripherally Inserted Central Catheters (PICC) 104 exists for clinical medical practice. A typical PICC is approximately 35 to 65 cm long (or as short as 20 to 25 cm), and between 0.5 and 2.0 mm outside diameter. PICCs are conventionally used to infuse a medication when the long term continuous infusion or repeated frequent infusions are desired. PICC catheters are often left in place for weeks and months.

Conventional PICCs generally have one or two internal lumens. The external surface of a PICC is usually marked with gradations allowing the user to gage the length of insertion. PICCs are made of silicone, polyurethane or other medical plastics. They are flexible so as to follow the path of a tortuous vein, but stiff enough to resist kinking when inserted into a vein. Prior to insertion of a PICC, the medical practitioner measures the distance from the site of insertion to the point, e.g., shoulder 168, on the body surface that approximately corresponds to the location where the tip 144 of the catheter is desired. The catheter length is trimmed to correspond to the distance between the catheter insertion point 138 on the skin and the desired tip location. The total tube length (i.e., the distance in the catheter traveled by the blood) for the catheter is generally no greater than 75 cm so as to avoid excessive flow resistance to the blood.

The medical practitioner inserts the catheter using a common medical technique, such as an "over the wire" method or through a hollow introducer needle that is later pealed apart and removed. If access to the right atrium is desired, the length of a typical PICC is 65 cm. If the catheter tip 144 is positioned in a basilic, axillary or cephalic vein at the level or just below the shoulder 168, it is often called a "mid-line" catheter and extends approximately 25 cm into the arm venous system.

It is not uncommon to place the tip 144 of the catheter in the subclavian vein in between the two lengths described above. Thus, PICC catheters can be inserted into peripheral veins at the elbow bend such that the tip of the catheter is beyond the venous flappers in the extremities of the vein. PICCs are typically used for infusion of medicine and infrequently for the withdrawal of small amounts of blood for blood tests. PICC dual lumen catheters that extend to the level of the shoulder or beyond have not been connected to blood pumps for the withdrawal of a continuous flow of blood or for purposes of Renal Replacement Therapy and particularly fluid removal by ultrafiltration.

A catheter similar to a common PICC may be used for the continuous access of blood for ultrafiltration. The rate of blood that can be withdrawn using a PICC catheter is sufficient to provide for clinically significant amount of ultrafiltration and provide relief to patients suffering from fluid overload. A PICC has sufficient length such that it extends beyond the venous flappers that would block retrograde flow. The length of the PICC can be selected by the medical practitioner so as to extend from the insertion point on the patient's arm, along the peripheral vein to a point near the shoulder where the peripheral vein no longer has venous flappers.

The PICC catheter 104 may be connected to an extracorporeal blood circuit 102 of a blood treatment system 100 for ultrafiltration or other RRT treatment. The system 100 may include a blood pump 108 that moves blood through the circuit 102 and applies a considerable (−100 to −300 mmHg) negative pressure to the PICC catheter. Most of this negative pressure serves to overcome the hydraulic resistance of the PICC tube to blood flow.

Figure 3:
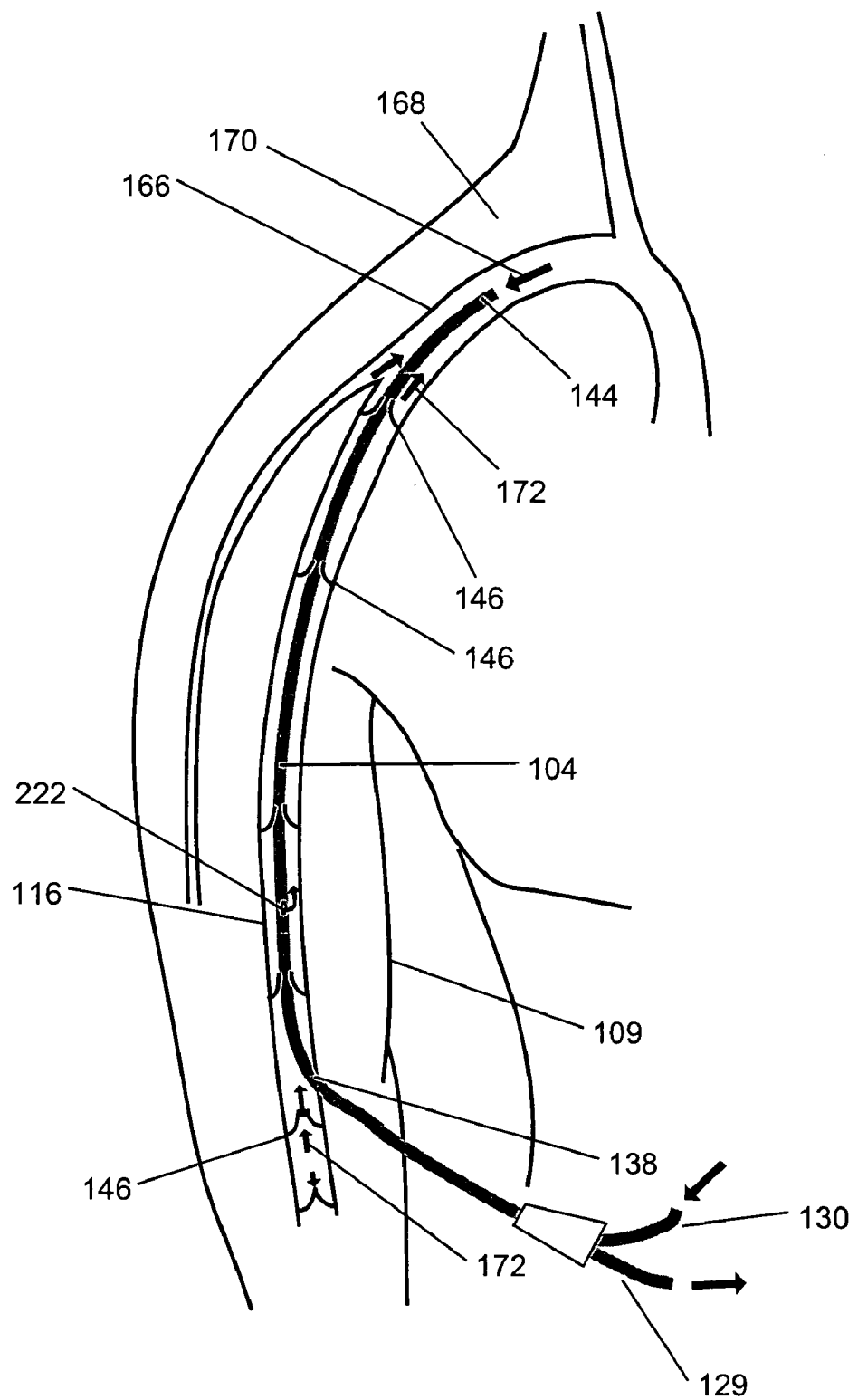
FIG. 3 is an illustration of a transverse section of a peripheral vein showing open and closed vein flapper valves and a dual lumen catheter inserted in the vein.

As shown in FIG. 3, the slight negative pressure at the tip of the PICC catheter causes retrograde blood flow 170 at the catheter tip 144, if the downstream blood flow 172 (antegrade) is insufficient. The retrograde flow supplements the antegrade flow so that there is a sufficient flow of withdrawn blood into the withdrawal PICC and to maintain sufficient pressure in the vein to prevent vein collapse.

The retrograde flow 170 in the vein draws blood through the vein from the central body venous blood supply, such as in the vena cava and other larger veins. By drawing blood using retrograde flow, the PICC 104 provides blood to the extracorporeal circuit at a rate greater than the rate that could be withdrawn using antegrade flow alone, which is a limitation of conventional methods using short phlebotomy needles. Accordingly, a PICC catheter has the double benefit of the safety, ease and comfort of peripheral vein access, and the high withdrawal flow rate available when using retrograde venous flows.

Moreover, a PICC extends the benefits of mechanical fluid removal by eliminating certain risks that previously limited its use. A PICC catheter 104 is inserted through a peripheral vein 116 in the patient's arm 109, in a manner only slightly more complex than the insertion of a common phlebotomy or IV medication needle. When inserted, the tip 144 of the PICC catheter resides in a larger venous vessel 166. Such larger venous vessels may be just below the shoulder, in the shoulder 168 or in a subclavian vein at or slightly above the shoulder. Even access to the vena cava or right atrium of the heart is not out of reach of certain long PICC catheters. Thus, the advantages of the retrograde blood flow, impossible with common catheter needles, become accessible using a PICC catheter.

The flapper valves 146 in peripheral veins 116 do not generally extend beyond the shoulder 168 of a person. By extending the tip 144 of a PICC catheter beyond the last venous flapper valve in a vein, there is no longer a natural barrier, e.g., flapper valves, separating the tip of the PICC catheter from a large supply of central blood. The blood withdrawal via a PICC catheter tip 144 is not limited to the antegrade blood flow 172 from venous drainage from capillaries in the hand and arm. The tip of the PICC catheter can also draw blood from substantially the entire cardiac output of the patient. This large supply of available blood at the tip of a PICC catheter should be sufficient for the operation of the extracorporeal apparatus. The blood from the large supply 166 of venous blood upstream of the flapper valves is drawn retrograde flow 170 into the catheter tip 144 by a reduced or negative pressure at the tip. Already, PICC catheters have been used by applicants in clinical trials to successfully relieve fluid from CHF patients that could not be successfully treated using a standard (non-dual lumen) withdrawal catheter.

An infusion port 222 in a side wall of the PICC catheter is positioned in the peripheral vein 116 and not far from the skin access site 138 used to insert the catheter. Treated blood, e.g., blood from which filtrate has been removed, is infused through the port 222 and into the vein 116. The infused blood flows in the vein and along the length of the portion of the catheter inserted in the vein and down stream of port 222. This length of catheter over which flows the infused blood may be a substantial portion of the inserted catheter length because as the port 222 is near the access site. The infused blood mixes with the blood flow 172 already in the vein and flowing outside of the catheter. The infused blood supplements the blood flow along the section of the vein 116 that sheaths the catheter. The supplemental blood flow increases the blood available to that section of the vein and to surrounding body tissue and helps avoid difficulties, e.g., vein collapse, that may raise due to lack of blood flow in that vein section. The infused blood flows along the vein towards the withdrawal tip 144. While a portion of the infused blood may be sucked into the withdrawal catheter tip, it is believed that the mixture of infused blood with blood naturally flowing in vein 116 mitigate any difficulties resulting by recirculation of blood through the blood circuit and such difficulties can be addressed by monitoring the Hct level of blood in the circuit and adjusting the filtrate rate to avoid excessive depletion of the Hct level of the blood flow in the peripheral vein 116.

Unlike conventional central venous catheters, PICCs can be inserted by non-surgeons. The process of inserting a PICC catheter is only slightly more complicated and requires only a bit more skill than does the placement of a standard catheter. However, non-surgical doctors, many skilled nurses and skilled physician assistants are or can be trained to insert PICC catheters. In modern hospitals thousands of nurses are currently trained to place PICC catheters. Moreover, PICC catheters may be inserted in emergency rooms, in clinics and in many other locations where there are medical persons trained to insert PICC catheters. Once the PICC catheter is inserted, the patient may rest comfortably in a bed or chair while blood is withdrawn. The extracorporeal blood circuit and associated device, such as an ultrafiltration device, need not be particularly large or complex. The blood circuit and device may be positioned on a stand next to the patient. The device may also be sufficiently automated so that it may be operated by most medical personnel (that are familiar with the operation of the device) and does not require constant operator attention.

The patient can sit or lie comfortably during the ultrafiltration, RRT or other blood treatment. During treatment, the patient may relax watching television or reading a book; talk to others in the room or by telephone, conduct light personnel or business work, such as computer or telephone operation, or do other light tasks normally done while sitting. Because there is only a small PICC withdrawal catheter and a return catheter inserted in a peripheral vein, the patient may be able to stand and move about a bit for comfort during treatment. In addition, the PICC catheter may remain in the patient between blood treatments (if the patient will have to have several treatments during the course of a few weeks).

Applicants conceived of and actually reduced to practice a blood circuit having a single lumen PICC catheter that overcomes the traditional problems associated with continuous blood withdrawal and return through PICC catheters. Applicants have demonstrated that PICC catheters and similar long catheters can be effectively and beneficially used to continuously withdrawal and return blood at rates sufficient for effective treatments, such as the removal of excess fluid in CHF patients. For example, a removal rate of excess fluid in a range of 250 to 750 mL/hr (or even in a range of 0.1 to 1.0 liters per hour) would be appropriate to relieve a fluid overload condition of CHF patients. To achieve this excess fluid removal rate, the blood flow through the filter may be no greater than 40–60 milliliters per minute which is about two percent of the total cardiac output of the patient. Applicants discovered that some of the dangers perceived with PICC catheters do not occur under the conditions associated with blood withdrawal and return for ultrafiltration. For example, a blood pump need only apply a negative pressure of 150 to 200 mmHg to draw blood through the PICC catheter. Blood gas bubbles occur at pressures of negative 500 mmHg, and lower.

In addition, applicants focused on treatments that may be successfully performed using the relatively low blood rates that can be achieved through a PICC. For example, ultrafiltration to relieve patients suffering from fluid overload requires blood flow rates of at least 10 mL/min. A blood flow rate of 40 mL/min can be achieved with the blood having hematocrit (volume fraction of red blood cells in blood) of 40%, through the PICC that is 35 cm long with the equivalent of a 1.1 mm internal diameter lumen. The PICC catheter equivalent internal diameter may be in a range of 0.9 to 1.2 mm. Under those conditions, a pressure drop of 180 mmHg across the PICC catheter should draw 40 mL/min of blood through the catheter. In addition to the pressure drop needed across the PICC catheter, the total negative pressure needed at the inlet of the pump depends on the pressure drop between the pump and the PICC catheter due to gravity and the resistance of blood circuit tube from the PICC catheter to the pump. A negative pump pressure of minus 250 mmHg is a reasonable estimate of the pressure needed to achieve a 180 mmHg pressure differential across the PICC catheter.

As shown in FIG. 1, the exemplary system described here is an ultrafiltration apparatus 100 designed for the extraction of plasma water (ultrafiltrate) from human blood. The apparatus may be equally applicable to extraction of ultrafiltrate from the blood of mammalian animals other than humans. Moreover, the apparatus may also be adapted to blood treatments other than ultrafiltration and to treatments that are in addition to ultrafiltration, such as the addition of drugs, solutions of electrolytes or other material to the blood.

The blood circuit 102 includes a blood filter 112; pressure sensors 152 (in withdrawal tube), 154 (in return tube) and 156 (in filtrate output tube); an ultrafiltrate collection bag 114 and tubing connectors to connect these components and form a continuous blood passage from the withdrawal lumen to the infusion lumen and an ultrafiltrate passage from the filter to the ultrafiltrate bag. The blood passage through the circuit is preferably continuous, smooth and free of stagnate blood pools and air/blood interfaces. The circuit may come in a sterile package and is intended that each circuit be used for a single treatment. The extracorporeal blood circuit 102 mounts on the console and, in particular, the blood pump 108 (for blood passage) and filtrate pump 150 (for filtrate output of filter). The circuit can be mounted, primed and prepared for operation within minutes by one operator.

To extract plasma water, the ultrafiltration system 100 includes a blood pump 108, a pump controller 110, and an extracorporeal blood circuit 102. The blood circuit is connected to the blood pump. The pump forces blood through a blood passage in the circuit. A filtrate pump 150 may be used to move filtrate from a filter 112 in the circuit to a filtrate bag 114. The blood passage includes a dual lumen catheter 104 that is inserted into a peripheral vein 116 near the skin surface of an extremity of the patient, such as an arm. The withdrawal lumen extension 221 is connected to a withdrawal blood circuit tube 118 via an airtight connector 120. The withdrawal tube may loop through a roller drive 122 of a roller pump 108. The end of the withdrawal tube is connected to a blood input port 124 of the filter 112. The filter has a blood output port 126 that is connected to an end of an infusion blood circuit tube 128. An opposite end of the infusion tube may be connected to an infusion lumen extension 220 of catheter 104 via an airtight connector 120.

The operator of the blood ultrafiltration apparatus, e.g., a nurse or medical technician, sets the maximum rate at which fluid is to be removed from the blood of the patient. A computer controller 110 in the pump console receives control inputs from the operator and sensor inputs from blood pressure sensors and blood leak detectors. The control inputs, e.g., settings, are entered into the blood pump console 148 using the user interface, which may include a display 158 and control panel 160 with control keys for entering maximum flow rate and other controller settings. Information to assist the user in priming, setup and operation is displayed on the LCD (liquid crystal display) 158. The controller includes a processor and electronic memory that stores programs to govern the pumps based on the control inputs and the sensor inputs.

The ultrafiltrate is withdrawn by the ultrafiltrate pump 150 into a graduated filtrate collection bag 114. When the bag is full, ultrafiltration stops until the bag is emptied. The controller 110 may determine when the bag is filled by calculating the amount of filtrate entering the bag based on the volume displacement of the ultrafiltrate pump in the filtrate tube and filtrate pump speed, or by receiving a signal indicative of the weight of the collection bag. As the blood is pumped through the circuit, an air detector 162 monitors for the presence of air in the blood circuit. A blood leak detector 163 in the ultrafiltrate output monitors for the presence of red blood cells in the ultrafiltrate. Signals from the air detector and/or blood leak detector may be transmitted to the controller, which in turn issues an alarm if a blood leak or air is detected in the ultrafiltrate or in the blood tubing of the extracorporeal circuit.

Regardless of the RRT modality desired, the basic principles of the apparatus design that are relevant to this invention remain the same. Blood that is withdrawn from the patient flows into the withdrawal tubing 118 and enters the blood passage of the blood circuit and is monitored by pressure sensor 152. Blood passes through the blood compartment 134 of the filter 112, and is returned to the patient via the return tube 128. Ultrafiltrate, effluent or dialysis solution passes through the filter casing surrounding the blood filled hollow fibers. These fibers have blood passages of approximately 0.2 mm. The walls of each fiber are porous, but retain blood solutes greater than 50,000 Daltons. Prior to return, blood passes through the pressure sensor 154 in the infusion tube. Pump 108 generates and controls the flow of blood, using the pressure sensor signals as a feedback signal. The filtrate pump 150 generates and controls the flow of ultrafiltrate. The ultrafiltrate tube 135 has a pressure sensor 156 that provides a feedback signal to the filtrate pump 150.

From the blood pump 108 to the filter 112, blood traverses through an air detector sensor 162 that will cause the pump to stop if air is detected in the blood circuit. An air bubble indicates a leak or break in the blood circuit. An air bubble can be dangerous if passed into the bloodstream of the patient. Accordingly, the detection of an air bubble will cause an alarm and stop the pumps. The blood leak detector 163 is a photometric device that uses infrared light beam to detect presence of red blood cells in the ultrafiltrate. The detection of blood in the ultrafiltrate tube indicates a filter failure because blood cells should not normally pass through the filter membrane into the filtrate tube. The blood and ultrafiltrate pressure sensors 152, 154, and 156 are included in the extracorporeal circuit 102 and are intended for one-time use. Air detector and blood leak detector are mounted on the system console and have means to clamp around the plastic tubing that forms the fluid passage.

Figure 4:
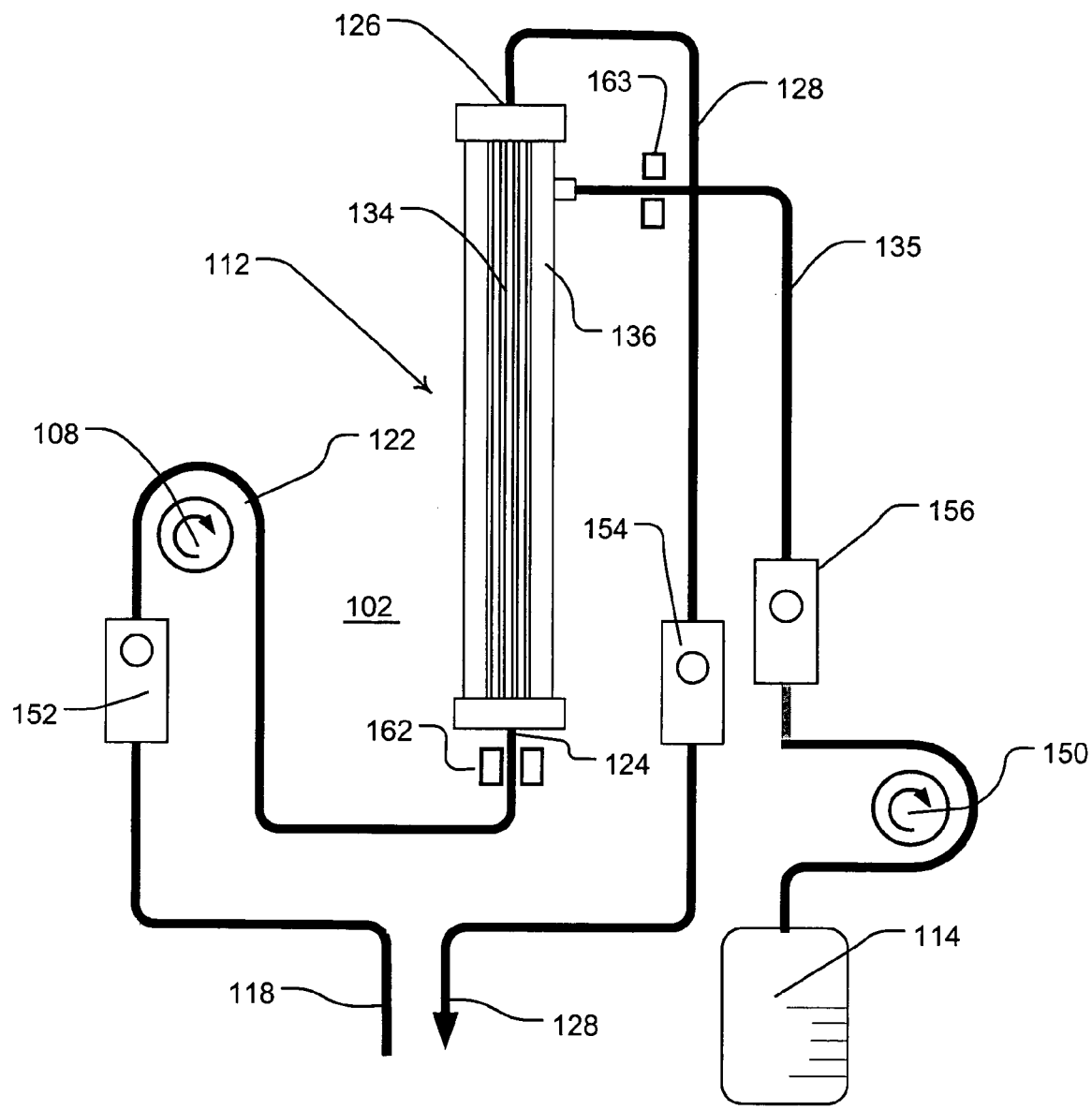
FIG. 4 is a schematic diagram showing a fluid path of blood and removed fluids for the blood circuit used with the blood ultrafiltration system shown in FIG. 1.

FIG. 4 shows a blood circuit 102 having a filter 112 that includes a blood compartment 134, e.g., a bundle of small tubes, having the blood inlet port 124 and the blood outlet port 126. The blood compartment 134 is separated by a filter membrane, porous walls of the small tubes, from a filtrate compartment 136 of the filter. The filter membrane is permeable to water and small molecules. The membrane is impermeable to blood cells, proteins and other large solutes particles. The patient 106, such as a human or other mammal, may be treated while in bed or sitting in a chair and may be conscious or asleep. The PICC catheter 104 may be attached to the patient in a hospital, doctor's office or an outpatient clinic (provided that adequate supervision of a doctor or other medically trained person is present).

To initiate ultrafiltration treatment, a cannula 104 for blood access is introduced into a suitable peripheral vein 116 at an insertion location 138 in the skin of the arm of the patient using an introducer needle (not shown), a guide wire (not shown) and other standard accessories using one of available and well-known medical techniques for introducing and localizing a peripherally inserted central catheter. For example, a guide wire may initially be inserted into a peripheral vein 116 in the arm of a patient and then slid through the vein by a skilled nurse, doctor or other train medical professional until the tip 144 of the PICC extends into the vein, e.g., one of an axillary vein, a subclavian vein, a vena cava, and a right atrium of the heart and beyond the last venous flapper 146. The location of the last venous flapper may be estimated by measuring, prior to insertion of the catheter, the distance on the surface patient's arm from the PICC insertion point to a location 166 in the veins just below the shoulder 168, which will be past the last flapper. The PICC can be cut or marked prior to insertion to indicate when it is been inserted far enough up the vein to extend beyond the last venous flapper 146.

If the insertion of the PICC 104 into the right atrium is desired, placement of the catheter is usually confirmed by an X-ray. The tip of the catheter is clearly visible on the x-ray, or other non-invasive inspection instrument. The output port of the infusion port may be difficult to see on an X-ray. A marker on the catheter and adjacent the infusion port is useful to locate that port in an X-ray. Confirmation of the location of the catheter tip and infusion port is useful because the wrong placement can result in the catheter tip being in the jugular vein (draining blood from the brain) of the patient. If a more common placement in the axillary or the subclavian vein is desired, visual confirmation of placement is not necessary. By properly-measuring the length of the catheter, the operator may be sufficiently confident that the catheter is positioned in the vein beyond the last venous flapper and not in a position where it can be dangerous to the patient. After positioning the catheter tip 144, the operator can draw a small amount of blood from the catheter using a syringe to ensure that the catheter is not kinked or placed in a dead-end in a small branch vessel. The same length measurement of the PICC typically ensures that the catheter is above the level of last flapper valve that does not typically extend beyond the shoulder. When the blood pump is started, if the computer controls (audible alarms, display screen 158 and/or the touch pad 160) of the pump console indicate to the operator that the blood flow is insufficient; the catheter can be carefully advanced several centimeters further into the vein to pass the valve.

FIG. 5 is a perspective view of a first embodiment of a dual lumen peripheral catheter 200 adapted for withdrawing blood from a central venous blood reservoir 166 and infusing the blood into the peripheral vein into which the catheter is inserted. FIG. 6 is an enlarged perspective view of the distal infusion lumen opening 222 of the catheter, and FIG. 7 is an enlarged perspective view of the distal withdrawal tip 144 of the catheter. At a proximal end, the catheter 200 includes a first air tight connectors 120 at an end 129 of the withdrawal lumen 212 and a second air tight connector 120 at an end 130 of the infusion lumen 214. These connectors 120 connect to the withdrawal tube 118 and infusion tube 128 of the blood circuit 102. Clamps 201, 202 on each of the withdrawal extension tubing 221 and infusion extension tubing 220 allow the operator to manually close and open these lumen. A hub 203 provides a coupling for the withdrawal extension tubing 221 and infusion extension tubing 220 and a mid-length dual lumen catheter tube 204. The withdrawal lumen 212 and infusion lumen 214 are created by the internal flow paths of the connectors 120, extension tubes 221, 220, hub 203, and catheter tubing 204.

FIG. 8 shows the catheter 200 in cross-section. FIG. 9 shows a view of the proximal end of the catheter. FIG. 10 shows the hub 203 in cross-section. FIG. 11 shows in cross-section the proximal region 11 having the infusion lumen opening 222 in a side wall of the catheter tube 204. FIG. 12 shows in cross-section the distal end region 12 of the catheter tube 204 showing the withdrawal lumen openings 236 in the side wall of the tube. FIG. 13 is a side view of the catheter 200 showing the corresponding locations for the cross-sectional drawings of the catheter tube 204 shown in FIGS. 14, 15 and 16.

Figure 21:
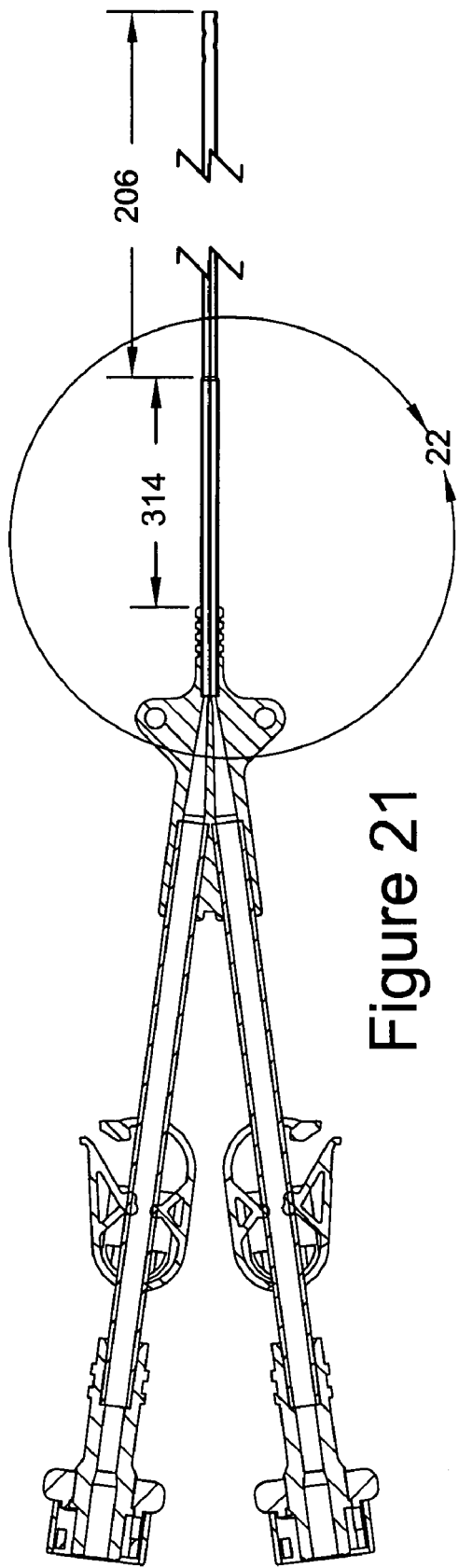
FIG. 21 is a cross-sectional view of a second embodiment of a dual lumen catheter having a greater diameter in the proximal dual lumen section than in a distal insertable dual lumen section.
Figure 22:
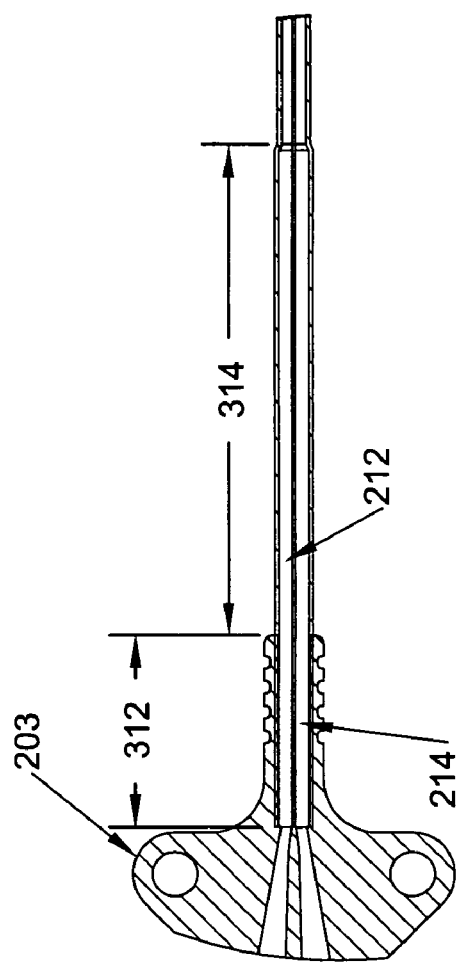
FIG. 22 is an enlarged cross-sectional view of the hub and large diameter section marked by region 22 in FIG. 21.

The tube 204 includes along its insertable length 206 a dual lumen section 208 and a single lumen section 228. The insertable length 206 may extend to the hub 203 or may only extend to a large diameter section 314 of the catheter, as is shown in FIGS. 21 and 22. The dual lumen section includes both a withdrawal lumen 212 and an infusion lumen 214. The single lumen section 228 includes the withdrawal lumen 212, but not an infusion lumen. The outer diameter (D) of the tube 204 preferably remains constant throughout the length 206 of the tube.

The longer the infusion lumen 214, the greater is the infusion pressure needed to pump blood from the blood circuit into the peripheral vein. To reduce the needed infusion pressure, the single lumen section 228 of the withdrawal lumen has a relatively large internal diameter and the length of the narrow diameter section 208 of the withdrawal lumen is short. The dual lumen section 208, which includes the withdrawal and infusion lumen, is preferably between 3 and 10 cm. This is an optimal range for insuring adequate infusion pressures as well as providing enough length for effective insertion and securement of the catheter in the peripheral vein.

The catheter tube 204 has a substantially uniform outside diameter along its insertable length 206, including along the dual lumen section 208, the transition section 230 from two lumens to a single lumen (see FIGS. 11 and 15), and the distal single lumen section 228. In particular, the tube 204 has a constant outside diameter throughout its insertable length 206, which is the tube section that is inserted through a peripheral vein. The size of the outside diameter (D) may be 1.5 millimeters (mm) to 2.0 mm to facilitate insertion into the vein by nursing staff and to enable adequate operation pressures for withdrawal and return of blood. The uniform outside diameter enables a maximization of the internal blood flow lumens throughout the insertable length 206 of the catheter which results in minimizing the resistance to flow.

The outlet(s) 222 of the infusion lumen 214 exit a sidewall in the catheter. The infusion lumen may terminate in a single opening 222 or a series of openings 222 that may be arranged within 2 cm of the distal end of the infusion lumen. The cross sectional area of the infusion outlet(s) 222 may be substantially equal to or greater than the cross sectional area of the infusion lumen in the insertable section, to prevent any significant increase in infusion pressure caused by the lumen opening(s). The orientation of the distal openings 222 may be straight as shown in FIGS. 17 and 18, or angled as shown in FIGS. 19 and 20. The angle of the openings 222 may match the end surface angle 232 of the infusion lumen 214. An angled orientation aids in manufacturing steps needed to create the openings 222 as well as minimizing turbulent flow as the infused blood flows through the openings 222 into the peripheral veins.

The distal opening 234 of the withdrawal lumen 212 may exit a blunt tip end 144 of the single lumen section 228 of catheter tube 204. The withdrawal lumen 212 may include a single opening 234 and/or multiple side wall openings 236 within 2 cm of the distal end of the tube. The total cross sectional area of the opening(s) 234 and 236 may be substantially equal to or greater than the cross sectional area of the withdrawal lumen 212 in the distal section 228 of the catheter tube 204 to prevent any significant increase in withdrawal pressure caused by the lumen opening(s). Alternatively, the fluid withdrawal lumen opening 234 may be through a tapered tip 144 such that the area of the withdrawal lumen opening 234 is greater than or equal to the lumen cross section.

The withdrawal lumen 212 internal cross sectional area is substantially greater along the distal single lumen section 228 of the catheter tube 204 than along the dual-lumen section 208. The cross-section of the withdrawal lumen expands in the transition region 230 where the infusion lumen terminates. Increasing the internal cross-sectional area of the withdrawal lumen in the distal section 228 reduces the flow resistance of the withdrawn blood flowing through that lumen. Because of the increase in cross-section, the insertable length of the single lumen section 228 may be extended to 20 cm or greater without creating excessive resistance in blood flows of up to 60 ml/min through the withdrawal lumen 212.

FIG. 14 shows the cross section of catheter tube 204 in the dual lumen section 208 which may be in cross-section a double-D configuration, having side-by-side the withdrawal lumen 212 and the infusion lumen 214. The lumens are separated by a septum wall that extends the length of the dual lumen section 208 of the catheter. Alternative cross-sectional configurations for the dual lumen section 208 including one lumen section being circular in cross-section and the other lumen being crescent in cross-section; both lumen being circular in cross-section with one lumen in the other; both lumens having elliptical cross-sections, and other cross-sectional shapes and arrangements of the lumens within the tube 204 may be suitable. The cross sectional areas of the two proximal lumens may be equal to simplify the manufacturing molding process. Unequal cross sections may be utilized in order to manipulate the operational pressures of the withdrawal 212 and infusion 214 lumens. An infusion lumen 214 cross sectional area of 0.5 to 0.8 $mm^2$ is preferred to maintain an infusion pressure below 300 mmHg.

The ability of the catheter lumens 212, 214 to remain fully open is useful for continuous peripheral vein blood withdrawal and infusion. There are several solutions that have been determined by the applicants to maintain flow through the catheter lumens. The geometric transition section 230 of the fluid withdrawal lumen cross section is extended over a length of 1–3 mm to prevent kinking. The durometer of the catheter tubing over the insertable length 206 is between and including 90–115 Shore A to prevent lumen pinching. Multiple tubing durometers, fillers, and material formulations may also be used to create reliable lumens to flow. The catheter durometer may be increased to 55–75 Shore D or made ridged in the area of the infusion opening 222 and the area within 1.5 cm proximally and distally of the infusion opening 222 to prevent kinking at the infusion opening 222. An overall region of no more than 3 cm ridged or semi-ridged tubing will prevent kinking at the opening 222 and also allow for easy insertion. Other methods such as imbedded coils, braids, durometer transitions, or combinations thereof, polymeric or metallic, may also be effective.

FIGS. 21 and 22 show region 22 of a dual lumen catheter in which the dual lumen sections 312 and 314 has a larger diameter for the portion that is not inserted into a vein than does the inserted dual lumen portion 206. The large diameter for the non-inserted length of the catheter further minimizes catheter resistance to flow. The internal diameter of the withdrawal lumen is large in the non-inserted portion 314 of the catheter, is relatively narrow in the dual lumen portion 206, and is large again in the single lumen section 228. It is preferred that the cross sectional areas of the withdrawal 212 and infusion 214 lumens be at least 10–20% larger in the distal hub section 312, than in the 206 section. Since this section 312 is not advanced into the skin insertion site, the resulting larger outside diameter does not present a restriction for the user to facilitate ease of insertion. To facilitate the assembly of this configuration the larger outside diameter may extend an additional 1–2 cm 314 of the tube beyond the distal hub section.

Figure 23:
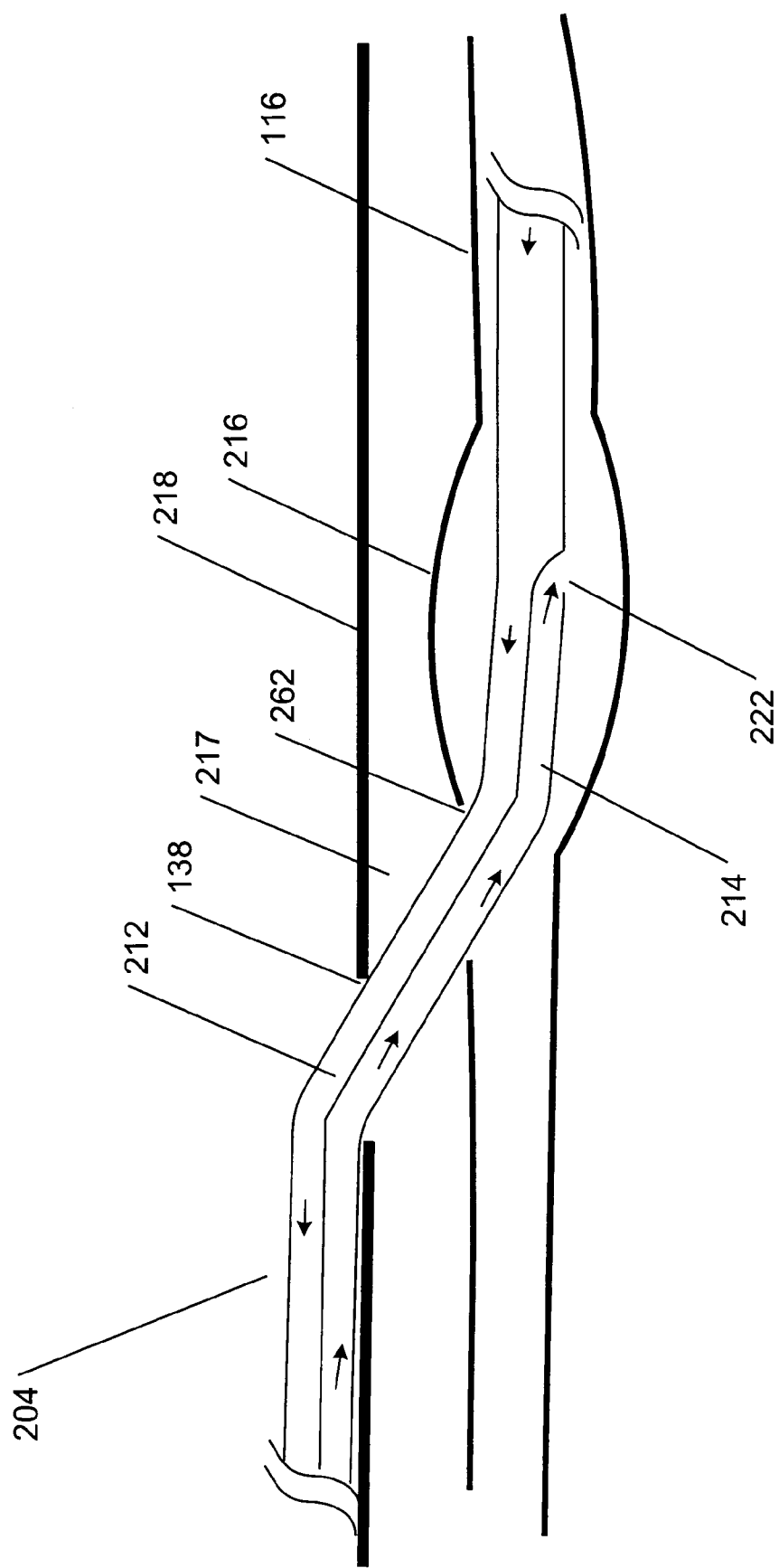
FIG. 23 is a schematic side view of a skin access site showing in cross-section a ballooning effect of blood infusion into a small peripheral vein.

Peripheral veins 116 can be up to 5–6 cm below the surface of the skin 218 in obese and fluid overloaded patients. As shown in FIG. 23, small peripheral veins 116 tend to balloon 216 when blood is infused at a rate of 10–60 ml/min. Blood infiltration or leakage into the arm tissue 217 can occur if the distal opening 222 of the infusion lumen 214 does not reach the vein 116 or is not adequately inserted into the vein such that the ballooning out section 216 of the vein reaches the vein puncture site 262. A length 208 of 3 to 10 cm from the hub 203 to the opening 222 of the infusion lumen 214 ensures that the opening 222 is positioned sufficiently distant into the vein and away from the vein puncture site 262 such that ballooning 216 should not cause blood leakage at the patient puncture site 138. To help identify the location of the infusion opening 222 of the infusion lumen a non-discrete mark 226 is placed within 0.5 cm of any edge of the opening 222. The mark 226 may be located visually prior to insertion and by X-ray or other non-invasive monitoring techniques.

Figure 24:
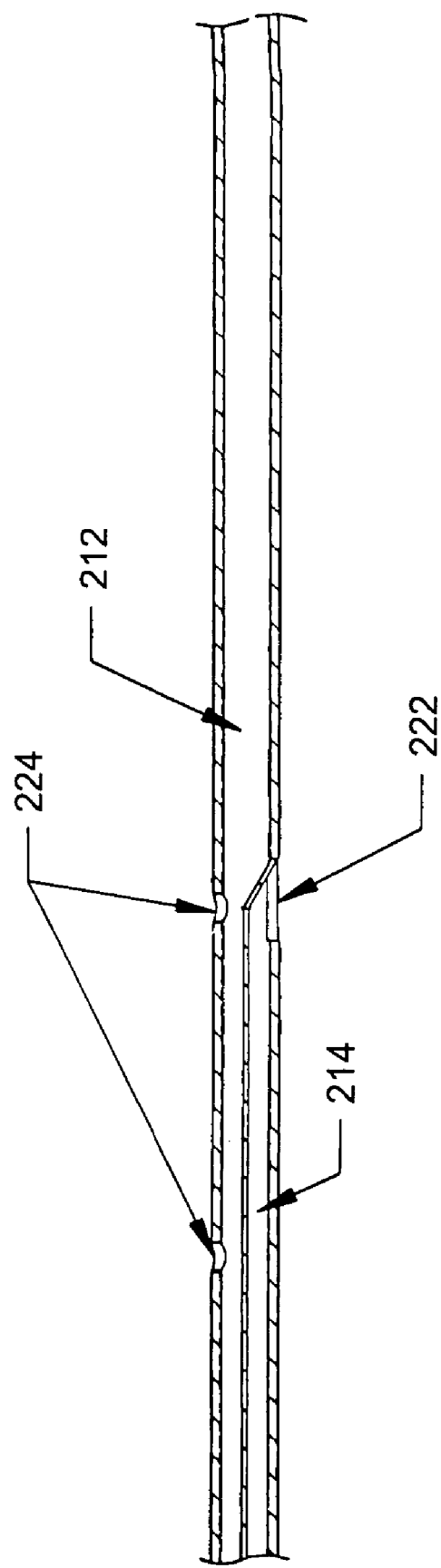
FIG. 24 is a cross-sectional view of another embodiment of a dual lumen catheter having a proximal withdrawal lumen opening(s) near the distal infusion lumen opening.

FIG. 24 shows blood withdrawal openings 224 in the withdrawal lumen proximate to the infusion opening 222. A known risk of extracorporeal blood therapy using two separate catheters is blood loss. It is possible for the return catheter to be dislodged from the patient while the withdrawal catheter is fully inserted into a vein. This creates the potential for uninterrupted blood withdrawal from the patient and the infusion of subsequent blood into the external environment, rather than into the vein of the patient. If a system pressure alarm does not occur and the condition is unnoticed, the patient could lose over 100 ml of blood in less than three minutes at a flow rate of 40 ml/min. The advantage of a dual lumen catheter is that if the catheter is removed then both the withdrawal and infusion lumens are removed. In this case even in the absence of a pressure alarm or the condition being unnoticed, air will be drawn into the system through at least withdrawal ports 234. An air detection alarm will be declared and the system automatically stopped with less than half of the 40 ml circuit volume lost. A dual lumen catheter can however be partially dislodged from the patient and result in the similar blood loss configuration as described in a two catheter system such that the withdrawal lumen tip 144 is located in vein 116 while the infusion lumen distal opening 222 is outside of the patient puncture site 138. The proximal withdrawal opening(s) 224 is placed in the withdrawal lumen 212 and is positioned an equal or lesser distance from the catheter hub 203 as the position of the most proximal infusion lumen opening 222. If the infusion lumen opening 222 is dislodged even partially from the patient insertion site 138 the withdrawal lumen opening 224 will be similarly pulled out of the vein. Because the withdrawal opening 224 is exposed to air, the air drawn into the system will trigger a pressure and/or air detection alarm, and the system automatically stopped.

Figure 25:
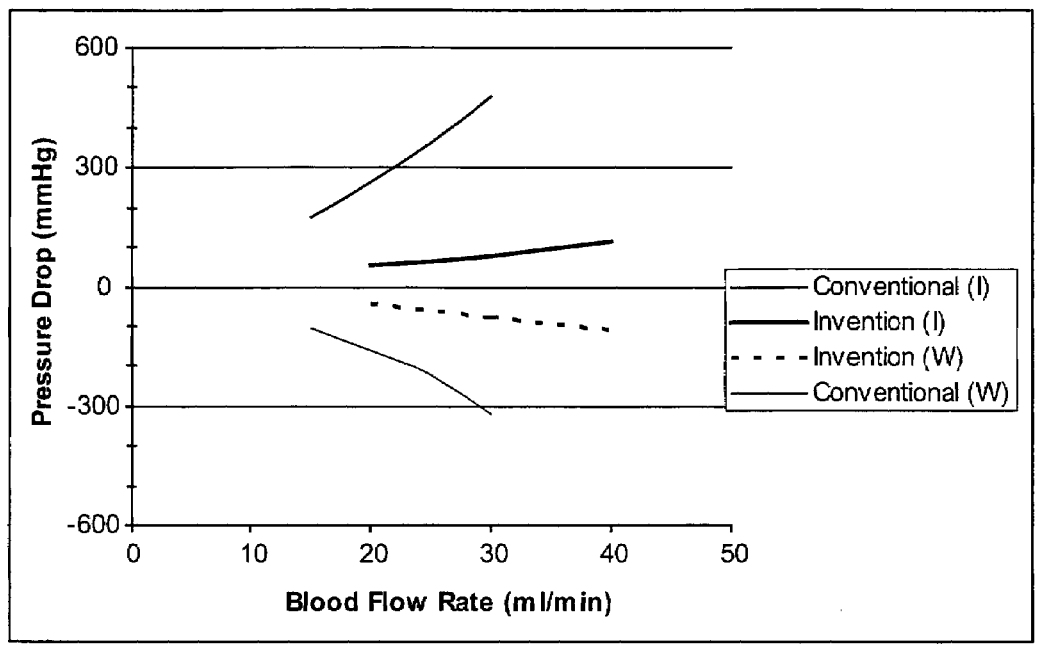
FIG. 25 is a graph of blood flow rate vs. pressure drop for conventional 6F midline catheters and the 6F invention catheter using 25% hematocrit blood.
Figure 26:
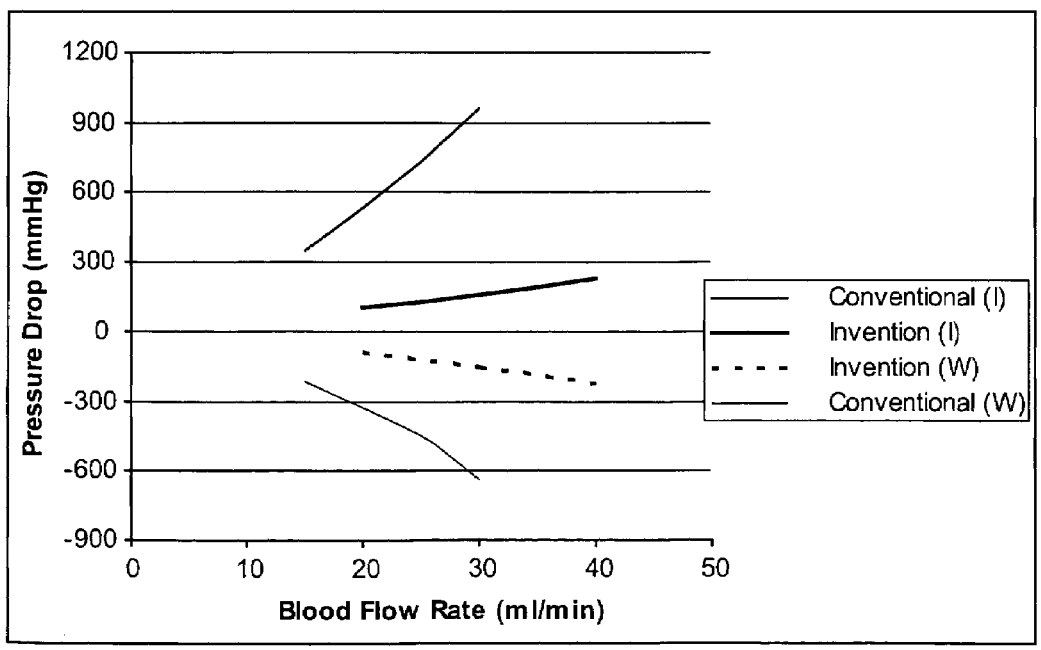
FIG. 26 is a chart of blood flow rate vs. pressure drop for conventional 6F midline catheters and the 6F invention catheter using 50% hematocrit blood.

FIGS. 25 and 26 show test data of comparative tests of a conventional mid-line 6F dual lumen catheter (normal weight lines) and the 6F catheter 200 (bold weight lines) described herein. Solid lines represent infusion (I) lumen data and doted lines represent withdrawal (W) lumen data. The comparative test results show how increasing the withdrawal lumen cross-sectional area in a distal section of a catheter and shortening the infusion lumen reduces the pressure drops through the lumens while maintaining the catheter outside diameter. The conventional catheter and inventive catheter 200 both had the same length of 35.0 cm and constant outside diameter of 2.0 mm. The conventional dual lumen catheter had constant internal lumen cross-sectional areas along the length of the catheter of 0.84 mm$^2$. The cross sectional areas of the lumens of the inventive catheter 200 was substantially the same as the conventional catheter for a proximal portion extending 7.4 mm from the hub to a transition point 230 where the withdrawal lumen cross sectional area increased to 1.59 mm$^2$ and the infusion lumen terminated.

The pressure drop in blood flow through a catheter lumen is primarily a function of catheter length and design, blood hematocrit, and blood flow rate. The level of blood hematocrit in CHF patients is typically 35–45% and almost always within 25%–50%. The hematocrit (Hct) value of blood was 25% for the test results shown in FIG. 25 and 50% for the test results shown in FIG. 26. The graphs plot blood flow rate through the catheter vs. the pressure drop across the catheter at hematocrit of 25 and 50 respectively. The graphs show that for the majority of patients, conventional designs create withdrawal (W) and infusion (I) pressures well beyond the desired operational range of ±300 mmHg. The conventional catheter design is limited to blood flows of approximately 20 ml/min or less in patients with a hematocrit of 25%. The 6F invention catheter results in pressure drops within the range of +300 mmHg at all points.

A feature of the dual lumen catheter 200 (in contrast to conventional designs) is the reversal of the location of the withdrawal and return lumen distal ends. The distal end 144 of the catheter is used for withdrawal and the proximal opening 222 is for infusion. The infusion opening(s) 222 is upstream in the vein to the withdrawal lumen openings 234, 236. As shown in FIG. 3, blood infused through the infusion opening 222 flows along the length of the catheter tube and passes over the withdrawal opening(s) 234, 236. Some of the infused blood may recirculate back into the withdrawal opening before the blood is circulated through the body of the patient. Conventional dialysis catheters avoid this configuration to avoid recirculation that could reduce the adequacy of the dialysis treatment.

Figure 27:
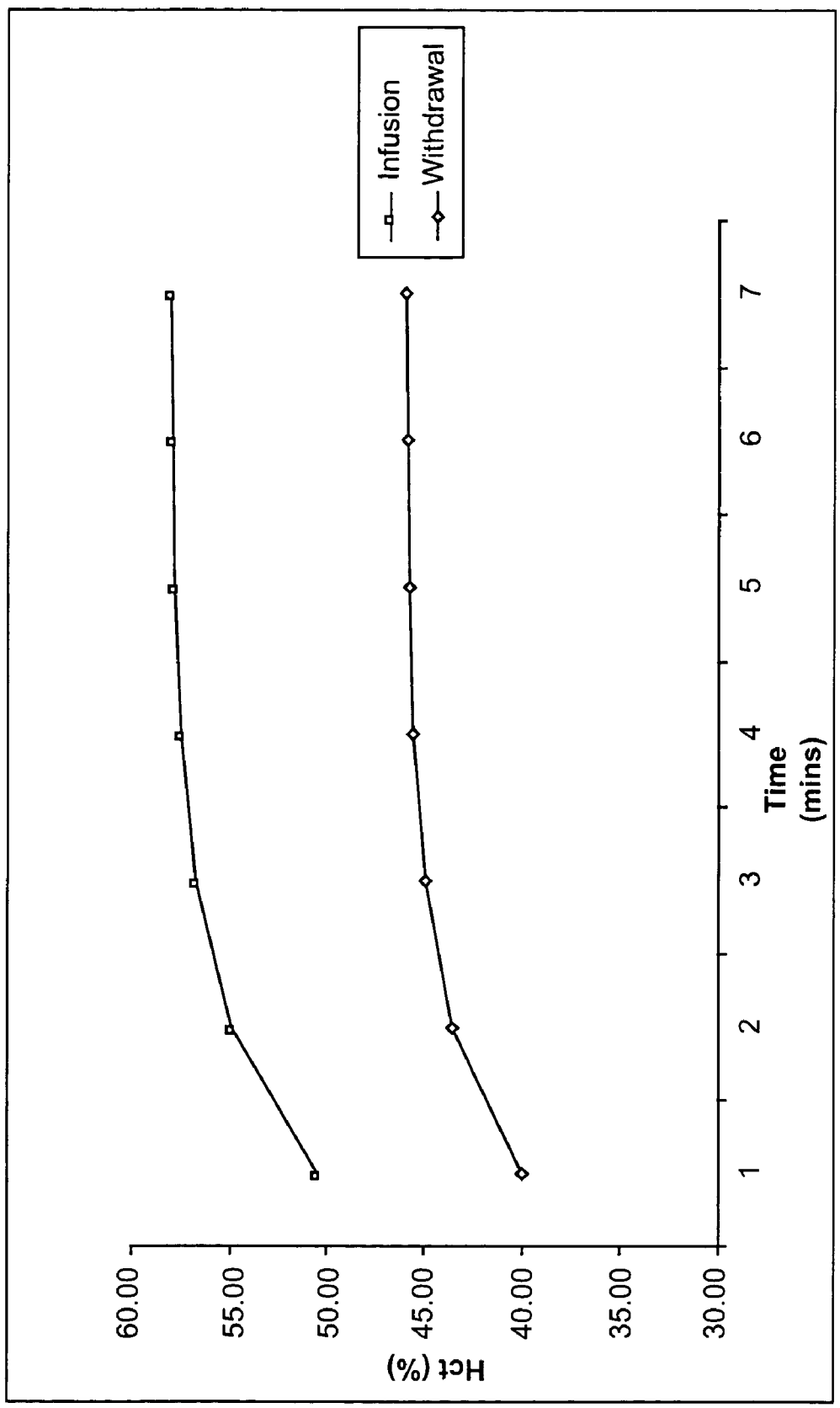
FIG. 27 is a graph showing the effect of blood recirculation rates on blood hematocrit (Hct) as a function of time.

While recirculation is not entirely desirable in ultrafiltration treatment, ultrafiltration can tolerate moderate levels of recirculation and still achieve therapeutic levels of fluid removal from the blood. FIG. 27 shows a graph of time vs. catheter withdrawal and infusion line hematocrit at a recirculation rate of 33%, a blood flow rate of 40 ml/min, and an ultrafiltrate rate of 500 ml/h. If 33% of the blood is being recirculated, the withdrawal blood Hct level will increase from 40% to 46% over time if the ultrafiltrate rate is set to 500 ml/hr. This time period for the rise in Hct is based upon the residence time of blood in the circuit. A recirculation rate of 33% implies that the blood exiting the infusion line will be entrained into the withdrawal line at a rate of 33% of withdrawal line blood flow. This will cause withdrawal blood flow to increase in Hct over time as the Hct of the blood exiting the infusion line increases until it stabilizes. A 33% entrainment rate will cause an Hct increase of 15% at an ultrafiltrate rate of 500 ml/hr. The charts presented in FIGS. 28 and 29 show how the recirculation of blood in the withdrawal line over various recirculation rates affects the withdrawal Hct at ultrafiltrate rates of 100 ml/hr and 500 ml/hr, respectively. The increases in Hct levels due to recirculation rates of up to 40% are tolerable for ultrafiltration. If the Hct level becomes too great, the ultrafiltrate rate can be dropped. The rise in withdrawal Hct will also decrease. A comparison of the charts shown in FIGS. 28 and 29 shows how the recirculation of blood in the withdrawal line over various recirculation rates affects the withdrawal Hct at a rate of 100 and 500 ml/hr. At an ultrafiltration rate of 100 ml/hr with a circulation rate of 40% the withdrawal Hct will only increase 3% above the patients base Hct. The disadvantage of increased Hct levels due to recirculation by having the withdrawal opening downstream of the infusion opening is outweighed by having the withdrawal opening positioned in a large supply 166 of blood and the infusion of extra blood in the peripheral vein having the catheter so as to reduce any potential of the vein to collapse on the catheter tube.

Figure 30:
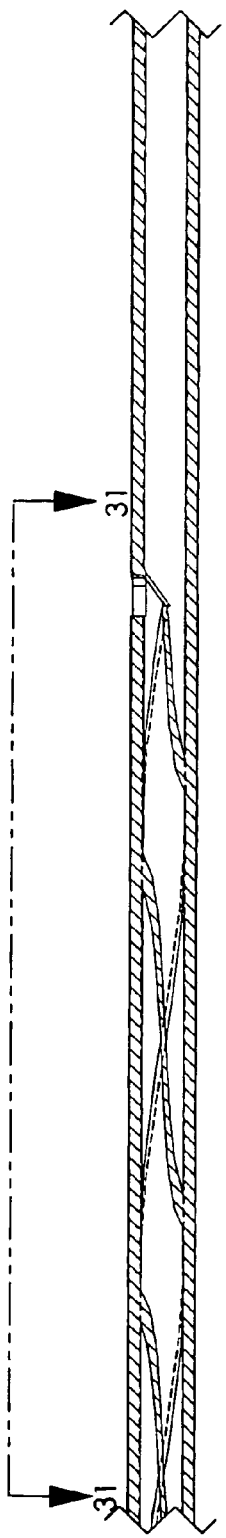
FIG. 30 is a cross-sectional view taken longitudinally along an axial length of a third embodiment of a dual lumen catheter having a twisted septum between the lumens.
Figure 31:
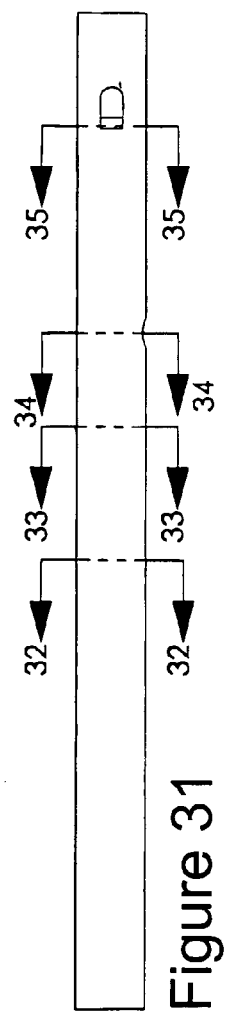
FIG. 31 is a side view of the third embodiment of the catheter along a portion of the catheter length corresponding to a distal portion of the infusion lumen, wherein the view is marked to indicate the locations on the catheter where the cross-section in taken for each of FIGS. 32 to 35.
Figure 35:
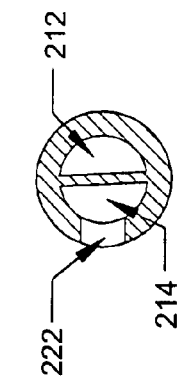
FIGS. 32 to 35 are cross-sectional views of the third catheter embodiment taken transversely through the catheter at the locations indicated in FIG. 31.
Figure 34:
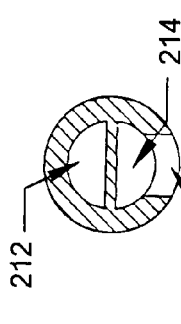
Figure 33:
Figure 32:
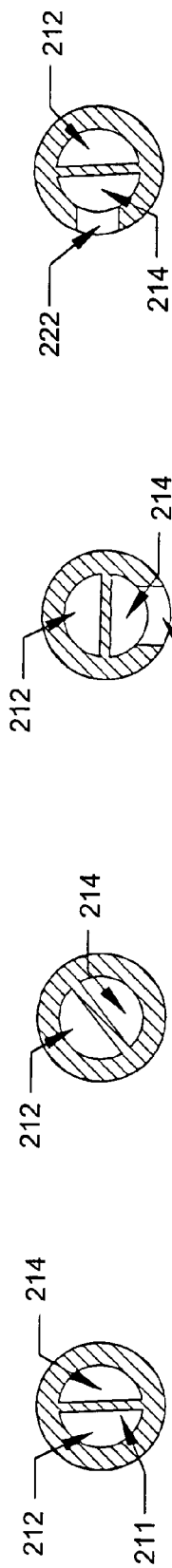
Figure 36:
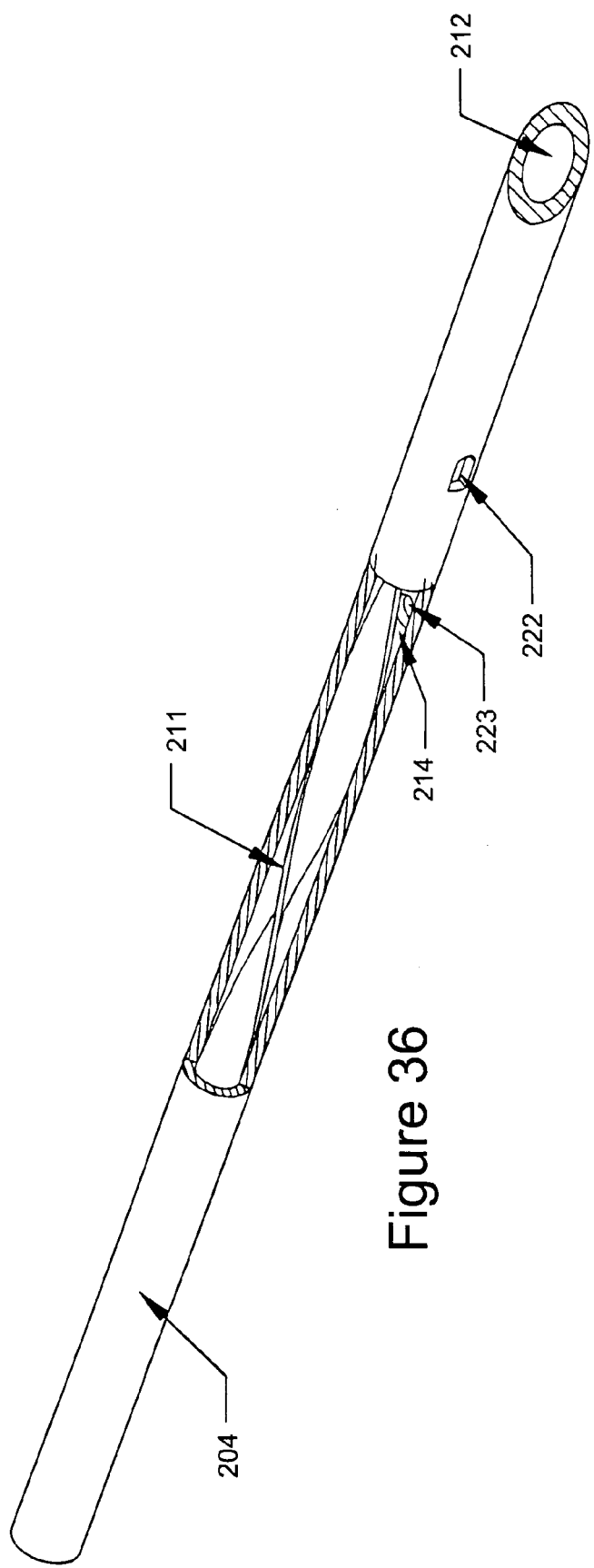
FIG. 36 is a perspective view of the third embodiment of the catheter showing a portion of the catheter cut away.

As is shown in FIGS. 30 and 36, the septum 211 separating the dual lumens may twist along its length. A helical septum 211 may be used to enable an additional infusion lumen opening 223 that is radially offset from the infusion lumen opening 222 by at least 60°. Offset infusion lumen openings prevent infusion lumen occlusion when one of the openings is against the vessel wall. The pitch of the helical septum can be continuous or varied along the length of the catheter to adjust catheter properties such as flexibility. The helical septum may a unitary part of the catheter or an additional component made from a polymer, metal or a combination of both. The helical portion of the septum may extend the length of the dual lumen portion of the catheter, or only be provided adjacent the openings 222,223.

FIGS. 37 to 40 show a coil reinforcing member 240 in the wall of the catheter along the transition 230 from the dual lumen to signal lumen sections. The reinforcing member 240 may be placed in a portion of the catheter between the proximal and distal regions or throughout the entire catheter length. The reinforcing member 240 can be a braid or coil. The braid pic rate or the coil pitch rate can be continuous or vary throughout the length of the catheter to change properties and/or provide openings in the catheter wall including the infusion distal opening 222 without severing the braid or coil, shown in FIG. 38. The catheter may have multiple openings in the wall for infusion 222 and withdrawal 236 which would be supported by a continuous reinforcing member 240. The reinforcing member 240 provides support to the catheter outer wall improving column strength, radial strength, kink resistance, and crush resistance. Additionally, the catheter wall thickness can be reduced increasing the cross sectional area of the lumens while minimizing the catheter outside diameter.

The reinforcing member 240 may be made from a metallic coil, metallic braid, polymer coil, polymer braid or combination. The cross sectional profile of the braid or coil material can be round, rectangular or other geometries. Furthermore, the reinforcing member 240 could have regions of a unique reinforcing member(s) 260 that do not wrap around the entire circumference of the catheter, shown in FIG. 39 and FIG. 40. The unique reinforcing member 260 may wrap around only a portion of the catheter circumference covering approximately 315° to 350° of the catheter cross section for a certain linear distance along the length which can create an opening for the infusion distal opening 222, shown in FIG. 39 and FIG. 40. The unique reinforcing member 260 can be placed in multiple places along the reinforcing member 240 and the reinforcing member 240 pitch and/or pic rate may change proximal and/or distal to the unique reinforcing member 260. The unique reinforcing member 260 can be part of the continuous reinforcing member 240, or made up of separate segment(s) that are loaded onto the catheter separately. For example, two coil segments may be embedded in the wall of the catheter tube at opposite ends of infusion distal opening 222, such that a gap between the coil segments is aligned with the opening 222.

The present invention has been described in terms of a particular embodiment(s). The invention is not limited to the disclosed embodiment(s). The scope of the present invention is defined by the spirit and scope of the claims that follow.

What is claimed is:

1. A method of withdrawal and return of blood in a patient undergoing extracorporeal blood treatment therapy comprising:
   a. inserting a dual lumen catheter into a surface peripheral vein in an extremity of the patient;
   b. advancing the catheter into a venous tree of the patient towards the heart a distance in a range of 20 centimeters (cm) to 45 cm;
   c. positioning a distal tip of the catheter beyond venous flappers in the venous tree;
   d. drawing blood from the catheter through an inlet opening in the distal tip;
   e. applying an extracorporeal treatment to the blood, and
   f. returning the treated blood to patient through the catheter.

2. A method as in claim 1 wherein the distal tip of the catheter is positioned in the venous tree in a shoulder region of the patient.

3. A method as in claim 1 wherein the treated blood is infused through an opening in the catheter and into the peripheral vein upstream in a blood flow moving towards the catheter tip.

4. A method as in claim 1 where the treatment is ultrafiltration and the catheter is positioned in the venous tree for a period of at least 4 hours.

5. A method as in claim 1 where the treatment is hemofiltration and the catheter is positioned in the venous tree for a period of at least 4 hours.

6. A method as in claim 1 where the treatment is dialysis and the catheter is positioned in the venous tree for a period of at least 4 hours.

7. A method as in claim 1 where the treatment is selected from a group consisting of: collecting platelet, collecting peripheral blood stem cells and performing a therapeutic aphaeresis procedure.

8. A method as in claim 1 where the catheter is inserted a length in a range of 20 cm to 45 cm into the peripheral vein and venous tree, and the treated blood is infused through an opening in the catheter at least 10 centimeters (cm) from an inlet to the catheter.

9. A method as in claim 1 where the insertion of the catheter is at an elbow level of an arm of the patient.

10. A method as in claim 1 wherein the catheter has a constant outside insertable diameter in a range of 1.5 millimeter (mm) to 2.3 mm.

11. A method as in claim 1 wherein the catheter has a total insertable tube length of no greater than 45 cm.

12. A method as in claim 1 wherein the dual lumen catheter further comprises a withdrawal lumen having a first cross-sectional internal lumen area along a dual lumen section and a second cross-sectional internal lumen area along a single lumen section distal to the dual lumen section, and wherein the second cross-sectional internal lumen area is at least 10% greater than the first cross-sectional internal lumen area.

13. A method as in claim 1 wherein the catheter has an infusion internal cross sectional lumen area in a range of 0.5 to and including 0.8 mm$^2$.

14. A method as in claim 1, wherein the catheter is inserted into a native peripheral vein.

15. A method as in claim 1 wherein the treated blood is returned at a location in the peripheral vein upstream in the venous tree of the position of the inlet opening into which blood is drawn, and further comprising recirculating a portion of the treated blood returned through the catheter by drawing the treated blood into the inlet opening as the treated blood flows through the venous tree and to the inlet opening.

16. A method as in claim 15 where an amount of recirculation is no greater than 33% of an amount of blood drawn into the inlet opening.

17. A method as in claim 1 wherein the treated blood is discharged from the catheter through a sidewall opening in the catheter.

18. A method as in claim 1 wherein the treated blood is discharged from an opening in the catheter and the opening is at least 10 cm upstream of the catheter from the inlet opening.

19. A method as in claim 1 wherein the treated blood is discharged from an opening in the catheter and the opening is at least 3 cm and no more than 10 cm distal from a catheter hub.

20. A method as in claim 1 wherein treated blood is discharged from an opening in an infusion lumen of the catheter and the opening has a cross sectional area at least equal to a cross sectional area of the infusion lumen in an insertable section of the catheter.

21. A method as in claim 1 wherein treated blood is discharged from a plurality of openings in an infusion lumen of the catheter and the openings have a combined cross sectional area at least equal to a cross sectional area of the infusion lumen in the insertable section of the catheter.

22. A method as in claim 1 wherein treated blood is discharged from an opening in an infusion lumen of the catheter and a non-discrete mark is located on said catheter within 0.5 cm of the opening.

23. A method as in claim 1 further comprising applying a reduced or negative pressure to a withdrawal lumen of the catheter to draw blood into the input opening.

24. A method as in claim 23 wherein the reduced pressure draws blood from the reservoir of blood in the patient upstream through the vein into the withdrawal catheter.

25. A method as in claim 1 further comprising applying a positive pressure to an infusion lumen of the catheter to move the treated blood and return the treated blood to the patient.

26. A method as in claim 1 where the extracorporeal treatment step further comprises: filtering blood drawing through the catheter to separate excess fluid from the blood, wherein filtered blood is the treated blood to be returned to the patient.

27. A method as in claim 26 wherein blood flow rate through a filter is less than two percent of a total cardiac output of the patient, and a flow rate of the excess fluid removed from the blood is at a rate no greater than 1.0 liters per hour.

28. A method as in claim 1 wherein a rate at which blood is withdrawn from the patient is no greater than 40 milliliters per minute.

29. A method as in claim 26, wherein a rate at which blood is withdrawn from the patient is in a range of 40 millimeters to 60 milliliters per minute, and a rate of removal of the excess fluid is at a rate no greater than 1.0 liters per hour.

30. A method as in claim 26, wherein the filtration is ultrafiltration.

31. A method as in claim 1, wherein the surface peripheral blood vessel is a basilic vein.

32. A method as in claim 1, wherein the surface peripheral blood vessel is a cephalic vein.

* * * * *